United States Patent
Deitz

(10) Patent No.: US 9,277,879 B2
(45) Date of Patent: Mar. 8, 2016

(54) SYSTEMS AND DEVICES FOR AN INTEGRATED IMAGING SYSTEM WITH REAL-TIME FEEDBACK LOOPS AND METHODS THEREFOR

(71) Applicant: ORTHO KINEMATICS, INC., AUSTIN, TX (US)

(72) Inventor: Adam Deitz, Austin, TX (US)

(73) Assignee: ORTHO KINEMATICS, INC., Austin, TX (US)

( * ) Notice: Subject to any disclaimer, the term of this patent is extended or adjusted under 35 U.S.C. 154(b) by 0 days.

(21) Appl. No.: 14/828,077

(22) Filed: Aug. 17, 2015

(65) Prior Publication Data

US 2015/0351667 A1    Dec. 10, 2015

Related U.S. Application Data

(62) Division of application No. 13/497,386, filed as application No. PCT/US2010/050210 on Sep. 24, 2010, now Pat. No. 9,138,163.

(60) Provisional application No. 61/245,984, filed on Sep. 25, 2009.

(51) Int. Cl.
| | |
|---|---|
| *G06K 9/00* | (2006.01) |
| *A61B 5/11* | (2006.01) |
| *G06T 7/00* | (2006.01) |
| *G06T 7/20* | (2006.01) |
| *A61B 5/055* | (2006.01) |
| *A61B 6/00* | (2006.01) |

(52) U.S. Cl.
CPC .............. *A61B 5/1128* (2013.01); *A61B 5/055* (2013.01); *A61B 6/505* (2013.01); *G06T 7/0012* (2013.01); *G06T 7/20* (2013.01)

(58) Field of Classification Search
CPC combination set(s) only.
See application file for complete search history.

(56) References Cited

U.S. PATENT DOCUMENTS

| | | | |
|---|---|---|---|
| 3,678,190 | A | 7/1972 | Cook |
| 4,210,317 | A | 7/1980 | Spann et al. |
| 4,404,590 | A | 9/1983 | Mayer et al. |
| 4,611,581 | A | 9/1986 | Steffee |
| 4,803,734 | A | 2/1989 | Onishi et al. |
| 4,805,602 | A | 2/1989 | Puno et al. |
| 4,922,909 | A | 5/1990 | Little et al. |

(Continued)

FOREIGN PATENT DOCUMENTS

| | | |
|---|---|---|
| AU | 2007238017 B2 | 3/2013 |
| DE | 20009875 U1 | 9/2000 |

(Continued)

OTHER PUBLICATIONS

Breen, et al. Lumbar spine motion palpation compared with objective motion analysis: preliminary findings. Euro. J. Chiro. 50: 27-32 (2002).

(Continued)

*Primary Examiner* — Anand Bhatnagar
(74) *Attorney, Agent, or Firm* — Shartsis Friese LLP; Cecily Anne O'Regan

(57) ABSTRACT

An integrated imaging system is invented for creating an optimal imaging session by importing information in real time from several sources and using that information to automatically and continuously adjust the parameters of the imaging session so as to create the optimal session for the prescribed testing session.

15 Claims, 17 Drawing Sheets

(56) References Cited

U.S. PATENT DOCUMENTS

| | | | |
|---|---|---|---|
| 5,000,165 A | 3/1991 | Watanabe | |
| 5,019,081 A | 5/1991 | Watanabe | |
| 5,058,602 A | 10/1991 | Brody | |
| 5,090,042 A | 2/1992 | Bejjani et al. | |
| 5,099,859 A | 3/1992 | Bell | |
| 5,129,900 A | 7/1992 | Asher et al. | |
| 5,203,346 A | 4/1993 | Fuhr et al. | |
| 5,220,614 A * | 6/1993 | Crain | G06K 9/00 348/128 |
| 5,224,176 A * | 6/1993 | Crain | G06K 9/00 382/136 |
| 5,316,018 A | 5/1994 | O'Brien | |
| 5,320,640 A | 6/1994 | Riddle et al. | |
| 5,330,417 A | 7/1994 | Petersen et al. | |
| 5,349,956 A | 9/1994 | Bonutti | |
| 5,400,800 A | 3/1995 | Jain et al. | |
| 5,414,811 A | 5/1995 | Parulski et al. | |
| 5,427,116 A | 6/1995 | Noone | |
| 5,442,729 A | 8/1995 | Kramer et al. | |
| 5,443,505 A | 8/1995 | Wong et al. | |
| 5,445,152 A | 8/1995 | Bell et al. | |
| 5,474,555 A | 12/1995 | Puno et al. | |
| 5,505,208 A | 4/1996 | Toomim et al. | |
| 5,548,326 A | 8/1996 | Michael | |
| 5,575,792 A | 11/1996 | Errico et al. | |
| 5,582,186 A | 12/1996 | Wiegand | |
| 5,582,189 A | 12/1996 | Pannozzo | |
| 5,590,271 A | 12/1996 | Klinker | |
| 5,640,200 A | 6/1997 | Michael | |
| 5,643,263 A | 7/1997 | Simonson | |
| 5,683,392 A | 11/1997 | Richelsoph et al. | |
| 5,688,274 A | 11/1997 | Errico et al. | |
| 5,690,630 A | 11/1997 | Errico et al. | |
| 5,707,643 A | 1/1998 | Ogura et al. | |
| 5,715,334 A | 2/1998 | Peters | |
| 5,725,527 A | 3/1998 | Biedermann et al. | |
| 5,740,267 A | 4/1998 | Echerer et al. | |
| 5,741,255 A | 4/1998 | Krag et al. | |
| 5,748,703 A | 5/1998 | Cosman | |
| 5,755,675 A | 5/1998 | Sihvonen | |
| 5,772,592 A | 6/1998 | Cheng et al. | |
| 5,772,595 A | 6/1998 | Votruba et al. | |
| 5,784,431 A | 7/1998 | Kalend et al. | |
| 5,797,911 A | 8/1998 | Sherman et al. | |
| 5,810,006 A | 9/1998 | Votruba et al. | |
| 5,813,406 A | 9/1998 | Kramer et al. | |
| 5,824,072 A | 10/1998 | Wong | |
| 5,838,759 A | 11/1998 | Armistead | |
| 5,863,293 A | 1/1999 | Richelsoph | |
| 5,879,350 A | 3/1999 | Sherman et al. | |
| 5,885,285 A | 3/1999 | Simonson | |
| 5,891,060 A | 4/1999 | McGregor et al. | |
| 5,891,145 A | 4/1999 | Morrison et al. | |
| 5,899,859 A | 5/1999 | Votruba et al. | |
| 5,931,781 A | 8/1999 | Boer | |
| 5,954,674 A | 9/1999 | Fuhr | |
| 5,964,760 A | 10/1999 | Richelsoph | |
| 6,002,959 A | 12/1999 | Steiger et al. | |
| 6,155,993 A | 12/2000 | Scott | |
| 6,298,259 B1 | 10/2001 | Kucharczyk et al. | |
| 6,412,620 B1 * | 7/2002 | Imura | G06K 9/00 194/317 |
| 6,428,490 B1 | 8/2002 | Kramer et al. | |
| 6,434,264 B1 | 8/2002 | Asar | |
| 6,497,672 B2 | 12/2002 | Kramer | |
| 6,560,476 B1 | 5/2003 | Pelletier et al. | |
| 6,726,691 B2 | 4/2004 | Osorio et al. | |
| 6,761,257 B2 * | 7/2004 | Karlsson | G07D 5/005 194/328 |
| 6,819,410 B2 * | 11/2004 | Adameck | G07D 5/005 356/71 |
| 6,866,643 B2 | 3/2005 | Kramer | |
| 6,890,312 B1 | 5/2005 | Priester et al. | |
| 6,907,280 B2 | 6/2005 | Becerra et al. | |
| 6,963,768 B2 | 11/2005 | Ho et al. | |
| 6,990,368 B2 | 1/2006 | Simon et al. | |
| 6,996,261 B2 | 2/2006 | deCharms | |
| 7,000,271 B2 | 2/2006 | Varadharajulu | |
| 7,153,307 B2 | 12/2006 | Scribner et al. | |
| 7,241,303 B2 | 7/2007 | Reiss et al. | |
| 7,266,406 B2 | 9/2007 | Kroeckel | |
| 7,418,076 B2 * | 8/2008 | Li | A61B 6/025 378/26 |
| 7,502,641 B2 | 3/2009 | Breen | |
| 7,679,971 B1 | 3/2010 | Yu | |
| 7,689,042 B2 | 3/2010 | Brunner et al. | |
| 7,780,703 B2 | 8/2010 | Yuan et al. | |
| 7,837,635 B2 | 11/2010 | Lissek et al. | |
| 7,916,281 B2 * | 3/2011 | Haddock | G07D 5/005 194/302 |
| 7,980,378 B2 * | 7/2011 | Jones | G06Q 20/1085 194/217 |
| 8,046,051 B2 | 10/2011 | Homan et al. | |
| 8,107,695 B2 | 1/2012 | Wollenweber | |
| 8,463,014 B2 | 6/2013 | Movassaghi et al. | |
| 8,615,123 B2 * | 12/2013 | Dabic | G07D 3/14 194/317 |
| 8,838,199 B2 * | 9/2014 | Simon | A61B 6/481 378/165 |
| 2002/0057828 A1 * | 5/2002 | Oosawa | G06T 7/60 382/132 |
| 2002/0085681 A1 * | 7/2002 | Jensen | A61B 5/06 378/197 |
| 2002/0120272 A1 | 8/2002 | Yuan et al. | |
| 2003/0081837 A1 | 5/2003 | Williame et al. | |
| 2003/0086596 A1 | 5/2003 | Hipp et al. | |
| 2003/0220648 A1 | 11/2003 | Osorio et al. | |
| 2003/0225327 A1 | 12/2003 | Willen et al. | |
| 2004/0003981 A1 * | 1/2004 | Lee | G07D 5/005 194/328 |
| 2004/0010260 A1 | 1/2004 | Scribner et al. | |
| 2004/0098803 A1 | 5/2004 | Schindler | |
| 2004/0141591 A1 | 7/2004 | Izuhara | |
| 2004/0172145 A1 | 9/2004 | Varadharajulu | |
| 2004/0225296 A1 | 11/2004 | Reiss et al. | |
| 2005/0107681 A1 | 5/2005 | Griffiths | |
| 2005/0148948 A1 | 7/2005 | Caputa | |
| 2005/0187459 A1 | 8/2005 | Trequattrini et al. | |
| 2005/0222505 A1 | 10/2005 | Damadian et al. | |
| 2005/0240193 A1 | 10/2005 | Layne et al. | |
| 2005/0259794 A1 | 11/2005 | Breen | |
| 2006/0020196 A1 | 1/2006 | Elias | |
| 2006/0032726 A1 * | 2/2006 | Vook | G07D 5/005 194/328 |
| 2006/0149136 A1 | 7/2006 | Seto et al. | |
| 2006/0185091 A1 | 8/2006 | Jackson | |
| 2006/0264952 A1 | 11/2006 | Nelson et al. | |
| 2007/0067034 A1 | 3/2007 | Chirico et al. | |
| 2007/0287900 A1 | 12/2007 | Breen et al. | |
| 2008/0039867 A1 | 2/2008 | Feussner et al. | |
| 2008/0125649 A1 * | 5/2008 | Meyer | A61B 6/0457 600/426 |
| 2008/0125678 A1 | 5/2008 | Breen | |
| 2009/0099481 A1 | 4/2009 | Breen | |
| 2010/0160775 A1 | 6/2010 | Pankratov et al. | |
| 2011/0270695 A1 * | 11/2011 | Jones | G06Q 20/1085 705/18 |
| 2012/0301009 A1 * | 11/2012 | Dabic | G07D 5/005 328/136 |
| 2012/0321168 A1 | 12/2012 | Deitz | |

FOREIGN PATENT DOCUMENTS

| | | |
|---|---|---|
| EP | 804032 A2 | 10/1997 |
| EP | 1219240 A2 | 7/2002 |
| EP | 1519681 B1 | 11/2006 |
| JP | 07284020 A2 | 10/1995 |
| WO | 2005007217 A2 | 1/2005 |
| WO | 2012082615 A2 | 6/2012 |

OTHER PUBLICATIONS

Breen, et al. Spine kinematics: a digital videofluoroscopic technique, J. Biomed. Engr. 11: 224-8 (1989).

(56) References Cited

OTHER PUBLICATIONS

Bryant. Method for determining vertebral body positions in the sagittal plane using skin markers. Spine 14(3): 258-65 (1989).

Carragee, et al. Low-pressure positive Discography in subjects asymptomatic of significant low back pain illness. Spine. 31(5): 505-509 (2006).

Cholewicki, et al. Method for measuring vertebral kinematics from videofluoroscopy. Clinical Biomechanics 6: 73-8 (1991).

Cholewicki, et al. Lumbar posterior ligament involvement during extremely heavy lifts estimated from fluoroscopic measurements. J. Biomechanics 25(1): 17-28 (1992).

Esses, et al. Kinematic evaluation of lumbar fusion techniques. Spine 21(6): 676-84 (1996).

Fujiwara, et al. The relationship between disc degeneration, facet joint osteoarthritis, and stability of the degenerative lumbar spine. J. Spinal Disorders 13: 444-50 (2000).

Harada, et al. Cineradiographic motion analysis of normal lumbar spine during forward and backward flexion. Spine 25: 1932-7 (2000).

Johnsson, et al. Mobility of the lower lumbar spine after posterolateral fusion determined by roentgen stereophotogrammetric analysis. Spine 15: 347-50 (1990).

Jones, Cervical spine cineradiography after traffic accidents. Archives of Surgery 85: 974-81 (1962).

Kaigle, al. et al Muscular and kinematic behavior of the lumbar spine during flexion-extension. Journal of Spinal Disorders. 11(2): 163-174 (1998).

Kleissen, et al., "Simultaneous Measurement of Surface EMG and Movements for Clinical USE" Med. Biol. Eng. Comp. 27( 3): 291-97 (1989).

Kondracki, Digital Videofluoroscopy, Manual Therapy 1, 146-48 (1996).

Lariviere, et al. A triaxial dynamometer to monitor lateral bending and axial rotation moments during static trunk extension efforts. Clin Biomech 16(1):80-3 (2001).

Lawrence, Disc degeneration. Its frequency and relationship to symptoms. Annals of Rheumatic Diseases 28:121-38 (1969).

Lee et al. Development and validation of a new technique for assessing lumbar spine motion, Spine 27(8): E215-20 (2002).

McGregor et al. Spinal motion in lumbar degenerative disc disease. J. Joint Surg (Br). 80-B: 1009-1013 (1998).

Quick, et al. Real-Time MRI of Joint Movement with True FISP, J. Mag. Res. Imaging 15(6):710-15 (2002).

Stokes, et al. Trunk muscular activation patterns and responses to transient force perturbation in persons with self-reported low back pain. Eur Spine J. 15:658-667 (2006).

Takayanagi, et al. Using cineradiography for continuous dynamic-motion analysis of the lumbar spine. Spine 26(17): 1858-1865 (2001).

Teyhen, et al., A New Technique for Digital Fluoriscopic Video Assessment of Sagittal Plane Lumbar Spine Motion, Spine vol. 30(14), pp. E406-E413 (2005).

Zheng, et al. Automatic Lumbar Vertebrae Segmentation in Fluoroscopic Images via Optimised Concurrent Hough Transform, 23rd Annual International Conf of IEEE Engineering in Med and Biology (2001).

* cited by examiner

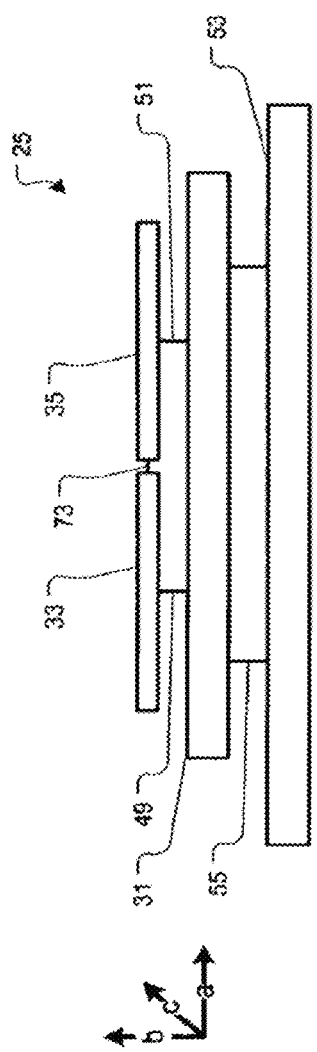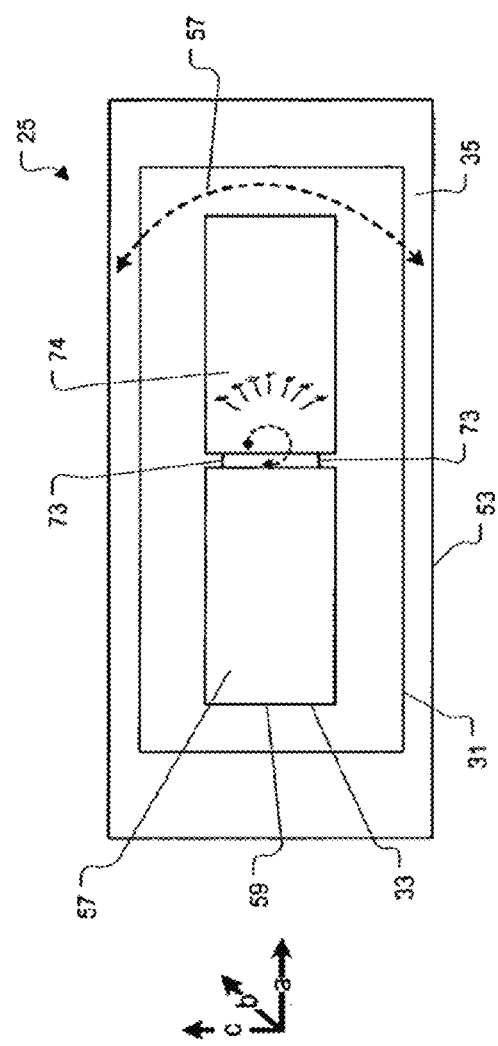

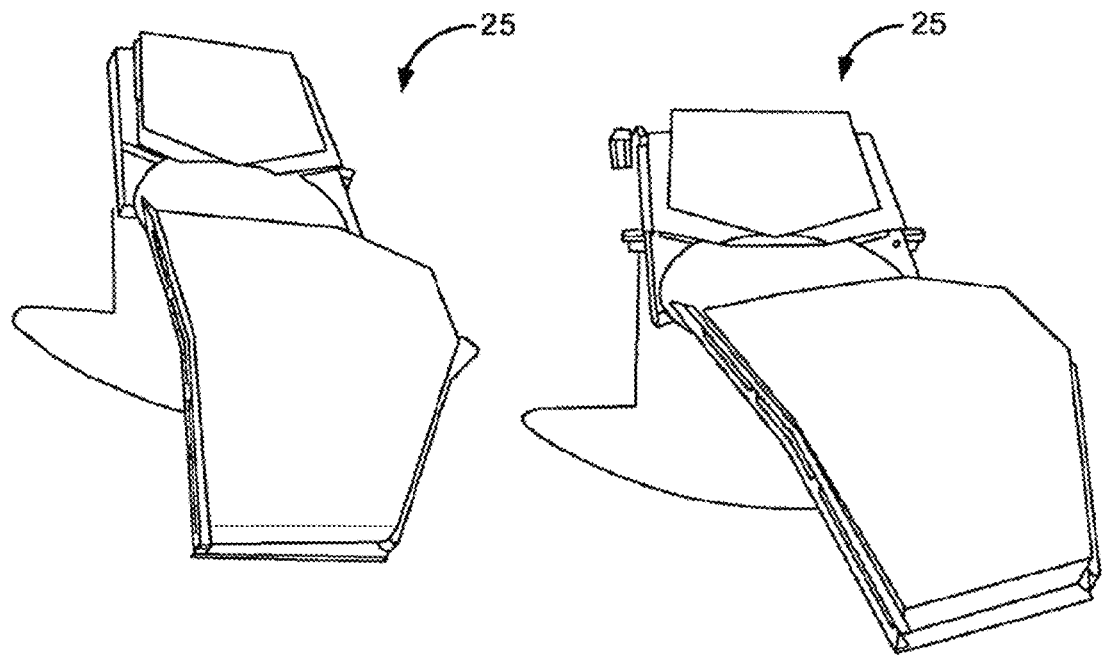
Fig. 5c
Fig. 5d
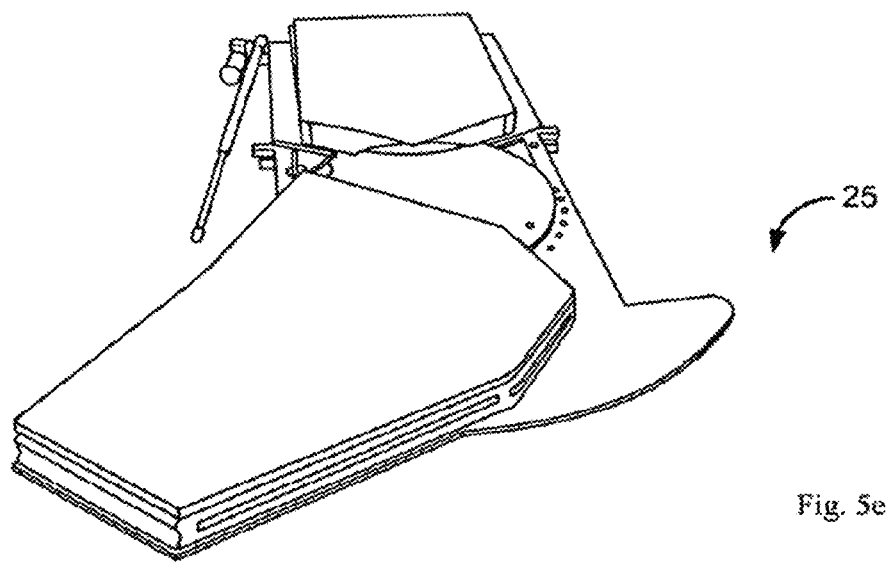
Fig. 5e

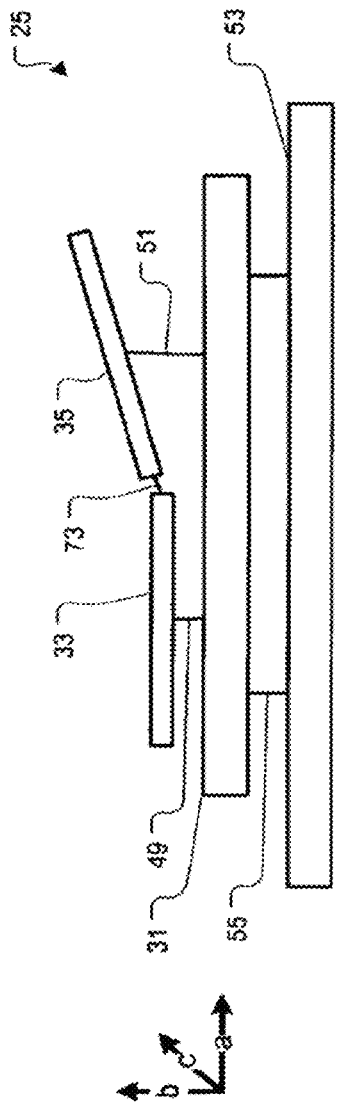
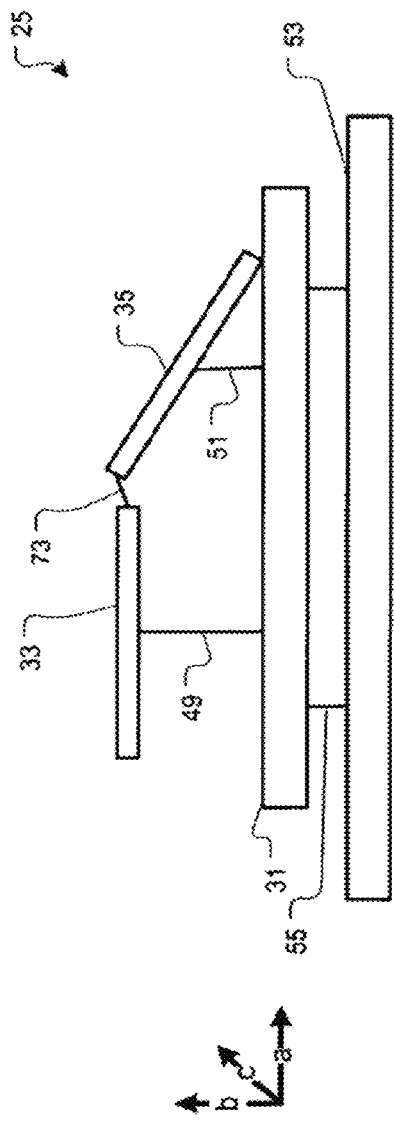
Fig. 6a
Fig. 6b

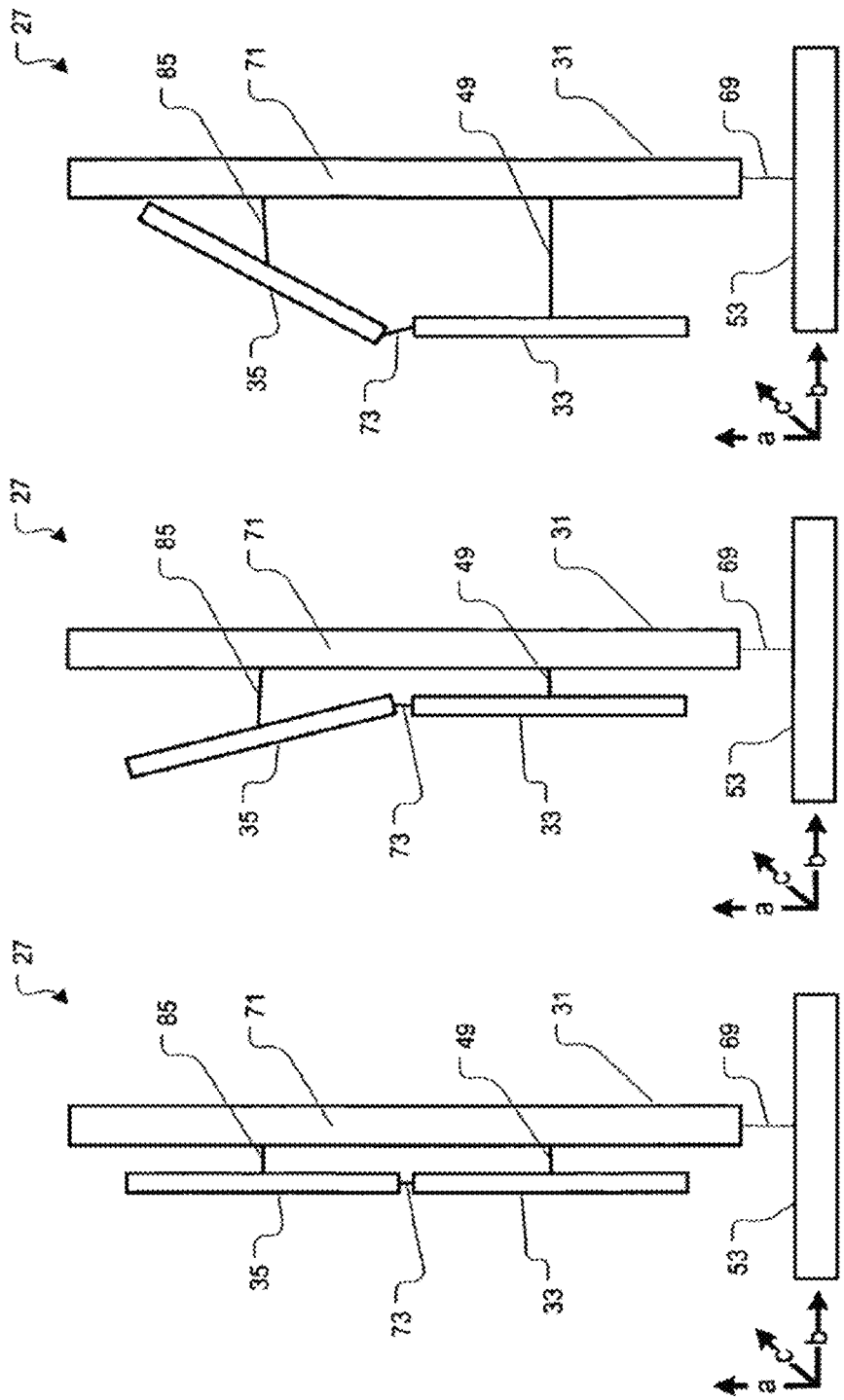

SYSTEMS AND DEVICES FOR AN INTEGRATED IMAGING SYSTEM WITH REAL-TIME FEEDBACK LOOPS AND METHODS THEREFOR

CROSS-REFERENCE

This application is a divisional application of U.S. patent application Ser. No. 13/497,386 filed on Jul. 9, 2012, under 35 USC §371, now U.S. Pat. No. 9,138,163 issued Sep. 22, 2015, which claims the benefit of International Application PCT/US2010/050210 filed on Sep. 24, 2010, under 35 USC §365, which claims the benefit of U.S. Provisional Application No. 61/245,984 filed Sep. 25, 2009, which applications are incorporated herein by reference.

BACKGROUND OF THE INVENTION

One of the most prevalent joint problems is back pain, particularly in the "small of the back" or lumbosacral (L4-S1) region. In many cases, the pain severely limits a person's functional ability and quality of life. Such pain can result from a variety of spinal pathologies. Through disease or injury, the vertebral bodies, intervertebral discs, laminae, spinous process, articular processes, or facets of one or more spinal vertebrae can become damaged, such that the vertebrae no longer articulate or properly align with each other. This can result in an undesired anatomy, loss of mobility, and pain or discomfort. Duke University Medical Center researchers found that patients suffering from back pain in the United States consume more than $90 billion annually in health care expenses, with approximately $26 billion being directly attributable to treatment. Additionally, there is a substantial impact on the productivity of workers as a result of lost work days. Similar trends have also been observed in the United Kingdom and other countries. As a result of this problem, increased funding is being applied toward developing better and less invasive orthopedic intervention devices and procedures.

Over the years the increased funding has led to the development of various orthopedic interventions. These include interventions suitable for fixing the spine and/or sacral bone adjacent the vertebra, as well as attaching devices used for fixation, including: U.S. Pat. No. 6,290,703, to Ganem, for Device for Fixing the Sacral Bone to Adjacent Vertebrae During Osteosynthesis of the Backbone; U.S. Pat. No. 6,547,790, to Harkey, III, et al., for Orthopaedic Rod/Plate Locking Mechanisms and Surgical Methods; U.S. Pat. No. 6,074,391, to Metz-Stavenhagen, et al., for Receiving Part for a Retaining Component of a Vertebral Column Implant; U.S. Pat. No. 5,891,145, to Morrison, et al., for Multi-Axial Screw; U.S. Pat. No. 6,090,111, to Nichols, for Device for Securing Spinal Rods; U.S. Pat. No. 6,451,021, to Ralph, et al., for Polyaxial Pedicle Screw Having a Rotating Locking Element; U.S. Pat. No. 5,683,392, to Richelsoph, et al., for Multi-Planar Locking Mechanism for Bone Fixation; U.S. Pat. No. 5,863,293, to Richelsoph, for Spinal Implant Fixation Assembly; U.S. Pat. No. 5,964,760, to Richelsoph, for Spinal Implant Fixation Assembly; U.S. Pat. No. 6,010,503, to Richelsoph, et al., for Locking Mechanism; U.S. Pat. No. 6,019,759, to Rogozinski, for Multi-Directional Fasteners or Attachment Devices for Spinal Implant Elements; U.S. Pat. No. 6,540,749, to Schafer, et al., for Bone Screw; U.S. Pat. No. 6,077,262, to Schlapfer, for Posterior Spinal Implant; U.S. Pat. No. 6,248,105, to Schlapfer, et al., for Device for Connecting a Longitudinal Support with a Pedicle Screw; U.S. Pat. No. 6,524,315, to Selvitelli, et al., for Orthopaedic Rod/Plate Locking Mechanism; U.S. Pat. No. 5,797,911, to Sherman, et al., for Multi-Axial Bone Screw Assembly; U.S. Pat. No. 5,879,350, to Sherman, et al., for Multi-Axial Bone Screw Assembly; U.S. Pat. No. 5,885,285, to Simonson, For Spinal Implant Connection Assembly; U.S. Pat. No. 5,643,263, to Simonson for Spinal Implant Connection Assembly; U.S. Pat. No. 6,565,565, to Yuan, et al., for Device for Securing Spinal Rods; U.S. Pat. No. 5,725,527, to Biederman, et al., for Anchoring Member; U.S. Pat. No. 6,471,705, to Biederman, et al., for Bone Screw; U.S. Pat. No. 5,575,792, to Errico, et al., for Extending Hook and Polyaxial Coupling Element Device for Use with Top Loading Rod Fixation Devices; U.S. Pat. No. 5,688,274, to Errico, et al., for Spinal Implant Device having a Single Central Rod and Claw Hooks; U.S. Pat. No. 5,690,630, to Errico, et al., for Polyaxial Pedicle Screw; U.S. Pat. No. 6,022,350, to Ganem, for Bone Fixing Device, in Particular for Fixing to the Sacrum during Osteosynthesis of the Backbone; U.S. Pat. No. 4,805,602, to Puno, et al., for Transpedicular Screw and Rod System; U.S. Pat. No. 5,474,555, to Puno, et al., for Spinal Implant System; U.S. Pat. No. 4,611,581, to Steffee, for Apparatus for Straightening Spinal Columns; U.S. Pat. No. 5,129,900, to Asher, et al., for Spinal Column Retaining Method and Apparatus; U.S. Pat. No. 5,741,255, to Krag, et al., for Spinal Column Retaining Apparatus; U.S. Pat. No. 6,132,430, to Wagner, for Spinal Fixation System; U.S. Pat. No. 7,780,703, and to Yuan, et al., for Device for Securing Spinal Rods.

Another type of orthopedic intervention is the spinal treatment decompressive laminectomy. Where spinal stenosis (or other spinal pathology) results in a narrowing of the spinal canal and/or the intervertebral foramen (through which the spinal nerves exit the spine), and neural impingement, compression and/or pain results, the tissue(s) (hard and/or soft tissues) causing the narrowing may need to be resected and/or removed. A procedure which involves excision of part or all of the laminae and other tissues to relieve compression of nerves is called a decompressive laminectomy. See, for example, U.S. Pat. No. 5,019,081, to Watanabe, for Laminectomy Surgical Process; U.S. Pat. No. 5,000,165, to Watanabe, for Lumbar Spine Rod Fixation System; and U.S. Pat. No. 4,210,317, to Spann, et al., for Apparatus for Supporting and Positioning the Arm and Shoulder. Depending upon the extent of the decompression, the removal of support structures such as the facet joints and/or connective tissues (either because these tissues are connected to removed structures or are resected to access the surgical site) may result in instability of the spine, necessitating some form of supplemental support such as spinal fusion, discussed above.

Other orthopedic interventional techniques and processes have also been developed to treat various spinal and joint pathologies. For example, U.S. Pat. No. 6,726,691 to Osorio for Methods and devices for treating fractured and/or diseased bone; U.S. Pat. No. 7,155,307 to Scribner for Systems and methods for placing materials into bone; U.S. Pat. No. 7,241,303 to Reiss for Devices and methods using an expandable body with internal restraint for compressing cancellous bone; and U.S. Patent Pubs. 2005/0240193 to Layne for Devices for creating voids in interior body regions and related methods; 2006/0149136 to Seto for Elongating balloon device and method for soft tissue expansion; 2007/0067034 to Chirico for Implantable Devices and Methods for Treating Micro-Architecture Deterioration of Bone Tissue; 2006/0264952 to Nelson for Methods of Using Minimally Invasive Actuable Bone Fixation Devices.

Health care providers rely on an understanding of joint anatomy and mechanics when evaluating a subject's suspected joint problem and/or biomechanical performance issue. Understanding anatomy and joint biomechanics assists in the diagnosis and evaluation of a subject for an orthopedic intervention. However, currently available diagnostic tools are limited in the level of detail and analysis that can be achieved. Typically, when treating joint problems, the intention is to address a specific structural or mechanical problem within the joint. For example, a surgeon might prescribe a spinal fusion procedure to physically immobilize the vertebra of a subject suffering from vertebral instability, or a physical therapist might prescribe exercises to strengthen a specific tendon or muscle that is responsible for a joint problem, etc.

It follows, therefore, that the extent to which a specific treatable joint defect can be identified and optimally treated directly impacts the success of any treatment protocol. Currently available orthopedic diagnostic methods are capable of detecting a limited number of specific and treatable defects. These techniques include X-Rays, MRI, discography, and physical exams of the patient. In addition, spinal kinematic studies such as flexion/extension X-rays are used to specifically detect whether or not a joint has dysfunctional motion. These methods have become widely available and broadly adopted into the practice of treating joint problems and addressing joint performance issues. However, currently available diagnostic techniques provide measurement data that is imprecise and often inconclusive which results in an inability to detect many types of pathologies or accurately assess pathologies that might be considered borderline. As a result, a significant number of patients having joint problems remain undiagnosed and untreated using current techniques, or worse are misdiagnosed and mistreated due to the poor clinical efficacy of these techniques.

For example, currently available techniques for conducting spinal kinematic studies are often unable to determine whether a joint dysfunction is a result of the internal joint structure per se, or whether the dysfunction is a result of, or significantly impacted by, the surrounding muscular tissue. Additionally, there are no reliable techniques for identifying soft tissue injury. Muscle guarding is a well established concept that is hypothesized to be highly prevalent among sufferers of joint pain, specifically that of the neck and back. In muscle guarding, a subject responds to chronic pain by immobilizing the painful area through involuntary muscle involvement. The ability to isolate different muscle groups is desirable to determine which muscle group or combination of groups, if any, could be contributing to, or responsible for, any joint dysfunction.

Additionally, the level of entrenchment of muscle guarding behavior cannot currently be determined. With respect to treatment decisions, the operative question in determining the level of "entrenchment" of any observed muscle guarding is to determine if the muscle guarding behavior is one which conservative methods of therapy could address through non-surgical therapy, or alternatively determining that the muscle guarding behavior so "entrenched" that such efforts would be futile and surgery should be considered.

In some instances, joint dysfunctions may not always present themselves in the movements traditionally measured during spinal kinematic studies such as flexion-extension and side-bending in either "full" non-weight-bearing or "full" weight-bearing planes of movement, which correspond to lying down and standing up postures respectively. Certain painful movements occur during joint rotation when the plane of rotation is somewhere between these two postures. Certain other painful movements only occur when the subject is rotating his or her spine while in a bent posture. In the case of vertebral motion in full weight-bearing postures, gravitational forces are relatively evenly distributed across the surface area of the vertebrae. However in postures where the subject is standing with his/her spine bent, gravitational forces are concentrated on the sections of the vertebrae located toward the direction of the bend. Detecting motion dysfunctions that occur only when in a standing bent posture requires the replication of joint motion in that specific bent posture in a controlled, repeatable, and measurable manner during examination.

Further, assuming that a system of measuring the surface motion of joints and the motion between internal joint structures that accounts for various types of muscle involvements would be possible, there would be a need for investigational data from controlled clinical trials to be collected across a broad population of subjects to afford for comparative analyses between subjects. Such a comparative analysis across a broad population of subjects would be necessary for the purpose of defining "normal" and "unhealthy" ranges of such measurements, which would in turn form the basis for the diagnostic interpretation of such measurements.

There have been significant technological innovations to the field of orthopedic interventions over the last few decades, specifically with the use of prosthetic and therapeutic devices to correct mechanical and structural defects of the bones and joints and to restore proper joint function. There have also been significant advances in the application of chiropractic and physical therapy approaches to correct muscle-, ligament-, and tendon-related defects. There has not however, been a corresponding improvement in the diagnostic methods used to identify proper candidates for these interventions. As a result, the potential impact and utility of the improvements in orthopedic intervention has been limited.

Imaging is the cornerstone of all modern orthopedic diagnostics. The vast majority of diagnostic performance innovations have focused on static images. Static images are a small number of images of a joint structure taken at different points in the joint's range of motion, with the subject remaining still in each position while the image is being captured. Static imaging studies have focused mainly on detecting structural changes to the bones and other internal joint structures. An example of the diagnostic application of static imaging studies is with the detection of spinal disc degeneration by the use of plain X-rays, MR images and discograms. However, these applications yield poor diagnostic performance with an unacceptably high proportion of testing events yielding either inconclusive or false positive/false negative diagnostic results (Lawrence, J. S. (1969) Annals of Rheumatic Diseases 28: 121-37; Waddell, G. (1998) The Back Pain Revolution. Edinburgh, Churchill Livingstone Ch2 p22; Carragee et al. (2006) Spine 31(5): 505-509, McGregor et al. (1998) J Bone Joint Surg (Br) 80-B: 1009-1013; Fujiwara et al. (2000(a)) Journal of Spinal Disorders 13: 444-50).

Purely qualitative methods for visualizing joint motion have been available for some time using cine-radiography (Jones, M. D. (1962) Archives of Surgery 85: 974-81). More recently, computer edge extraction of vertebral images from fluoroscopy has been used to improve this visualization for use in animations (Zheng et al. (2003) Medical Engineering and Physics 25: 171-179). These references do not, however, provide for any form of measurement or identification of objectively defined motion abnormalities, and therefore is of very limited diagnostic value other than in the detection of grossly and visibly obvious abnormalities that would be detectable using static image analysis methods. Without any quantitative or objective measurement parameters defined, it is impossible to utilize such approaches in comparative analyses across wide populations of subjects, which is required for the purpose of the producing definitive diagnostic interpretations of the results as being either "normal" or "unhealthy". Further, there have been no diagnostically useful validations of qualitative motion patterns that are generally absent in non-sufferers but present in subjects suffering from known and specific joint functional derangements or symptoms, or vice versa.

A method for determining vertebral body positions using skin markers was developed (Bryant (1989) Spine 14(3): 258-65), but could only measure joint motion at skin positions and could not measure the motion of structures within the joint. There have been many examples skin marker based spine motion measurement that have all been similarly flawed.

Methods have been developed to measure changes to the position of vertebrae under different loads in dead subjects, whose removed spines were fused and had markers inserted into the vertebrae (Esses et al. (1996) Spine 21(6): 676-84). The motion of these markers was then measured in the presence of different kinds of loads on the vertebrae. This method is, however, inherently impractical for clinical diagnostic use. Other methods with living subjects have been able to obtain a high degree of accuracy in measuring the motion of internal joint structures by placing internal markers on the bones of subjects and digitally marking sets of static images (Johnsson et al. (1990) Spine 15: 347-50), a technique known as roentgen stereophotogrammetry analysis (RSA). However RSA requires the surgical implantation of these markers into subjects' internal joint structures, requires the use of two radiographic units simultaneously, and requires a highly complicated calibration process for every single test, and therefore is too invasive and too cumbersome a process for practicable clinical application.

Cine-radiography of uncontrolled weight-bearing motion (Harada et al (2000) Spine 25: 1932-7; Takavanagi et al. (2001) Spine 26(17): 1858-1865) has been used to provide a set of static images to which digital markers have been attached and transformed to give quantitative measurement of joint motion. Similar measurement of joint motion has been achieved using videofluoroscopy (Breen et al. (1989) Journal of Biomedical Engineering 11: 224-8; Cholewicki et al. (1991) Clinical Biomechanics 6: 73-8; Breen et al. (1993) European Journal of Physical Medicine and Rehabilitation 3(5): 182-90; Brydges et al. 1993). This method has also been used to study the effects on joint motion of weightlifting (Cholewicki, J. and S. M. McGill (1992) Journal of Biomechanics 25(1): 17-28). The prior art using this method involves a manual process in which internal joint structures are marked by hand with digital landmarks on digital image files of consecutive frames of videoflouroscopy recordings of a subject's joint motion. A computer then automatically determines the frame-to-frame displacement between such digital landmarks to derive quantitative measurements of the motion of joint structures (Lee et al. (2002) Spine 27(8): E215-20). Even more recently, this approach has been accomplished using an automatic registration process (Wong et al. (2006) Spine 31(4): 414-419) that eliminates the manual marking process and thus reduces the laboriousness of the previous processes. However both of these methods, as well as all of the other methods mentioned in this paragraph, studied the motion of joints based on the imaging of uncontrolled, weight-bearing body motion.

Using uncontrolled, weight-bearing motion to derive quantitative measurements of joint motion confounds the diagnostic interpretation of such measurements so as to render them diagnostically useless. The diagnostic interpretation of such measurements would normally be based on a comparative analysis of joint motion measurements across a wide population of subjects, and would strive to identify statistically significant differences in these measurements between "normal" and "unhealthy" subjects, such that any given subject can be classified as "normal" or "unhealthy" based on that subject's joint motion measurement values. For such purposes, it is necessary to reduce the background variability of measurements across tested subjects as much as possible, so that any observed difference between "normal" and "unhealthy" subjects can be definitively attributable to a specific condition. Not controlling the motion that is being studied introduces variability into these comparative analyses due to differences that exist across testing subjects with respect to each subject's individual range of motion, symmetry of motion, and regularity of motion. These differences affect the joint motion of each subject differently, and collectively serve to create wide variability among joint motion measurements across subjects. Controlling for these factors by ensuring a consistent, regular, and symmetric body part motion during diagnostic testing serves to minimize the effects of these factors on a subject's relevant joint motion measurements, thereby reducing the variability of such measurements across subjects and therefore increasing the likelihood that such measurements will yield useful diagnostic results.

In addition to failing to control motion during testing, not accounting for the involvement and effects of muscles that are acting when a subject moves under their own muscular force while in a weight-bearing stance further adds to this variability by introducing such inherently variable factors such as the subject's muscle strength, level of pain, involuntary contraction of opposing muscle groups, and neuro-muscular coordination. Taken together, all of these sources of variability serve to confound diagnostic conclusions based on comparative analyses by making the ranges of "normal" and those of "abnormal" difficult to distinguish from one another other in a statistically significant way. Such an inability to distinguish between "normal" and "unhealthy" subjects based on a specific diagnostic measurement renders such a measurement diagnostically useless, as has been the case heretofore in the prior art which has focused on measurements of uncontrolled joint motion measured in subjects in weight-bearing postures and moving their joints through the power of their own muscles and in an uncontrolled fashion.

U.S. Pat. No. 7,000,271 discloses a tilting table capable of some movement to keep an iso-center at a fixed position. U.S. Pat. No. 7,343,635 describes a multi-articulated tilting table which positions and supports a subject during examination and treatment. U.S. Pat. No. 7,502,641 to Breen discloses a device for controlling joint motion and minimizing the effects of muscle involvement in the joint motion being studied. This device minimizes variability among joint motion measurements across wide populations of subjects. As a result, comparative analyses of such measurements can be performed to determine statistical differences between the motion of "normal" and "unhealthy" subjects which in turn can provide a basis for determining the statistical confidence with which any given subject could be considered "normal" or "unhealthy" based solely on joint motion measurements.

U.S. Pat. No. 5,505,208 to Toomin et al. developed a method for measuring muscle dysfunction by means of collecting muscle activity measurements using electrodes in a pattern across a subject's back while having the subject perform a series of poses where measurements are made at static periods within the movement. These electromyographical readings of "unhealthy" subjects were then compared to those of a "normal" population so as to be able to identify those subjects with abnormal readings, however does not provide for a method to report the results as a degree of departure from an ideal reading, instead can only say whether the reading is "abnormal". U.S. Pat. No. 6,280,395 added an additional advantage to this method for determining muscle dysfunction by using the same method, yet adding the ability to better normalize the data by employing a more accurate reading of the thickness of the adipose tissue and other general characteristics that might introduce variability into the readings, as well as the ability to quantify how abnormal a subject's electromyographical reading is as compared to a "normal" population.

Joint muscle activity has been evaluated using electromyography in combination with some type method or device to track the surface motion of the joint. In one study, visual landmarks were used to help the subject more consistently reproduce a tested motion so as to standardize the joint motion and eliminate variability. (Lariviere, C 2000) However, visual land marking methods to not yield as "standardized" a motion as can be achieved with motion that is mechanically controlled, and measurements of the motion of internal joint structures based on surface motion measurements are too variable to be of significant clinical utility.

Another study used electromyography in conjunction with the use of a goniometer, a device that measures the surface motion of external body parts so as to link the muscle activity signals with precise surface motion measurements. (Kaigle et al. (1998) Journal of Spinal Disorders 11(2): 163-174). This method however does not take into consideration the motion of internal joint structures such that a determination as to the specific cause of joint dysfunction cannot be evaluated.

Electromyographic measurements taken during weight-bearing joint motion, with simultaneous recording of the motion of the body part using goniometers and also with simultaneous recordings of the motion of internal joint structures through the tracking of surgically-implanted metal markers, has been used to correlate muscle activity with the motion of joints and internal joint structures (Kaigle, supra). However this approach studied joint motion that was uncontrolled and required an invasive surgical procedure to place the metal markers, and thus were neither useful nor feasible for clinical diagnostic application.

Electromyography has also been used in conjunction with a device that provides transient force perturbation so as to observe whether there is a difference between subjects with low back pain and those without low back pain to determine how their muscles respond to such a force. (Stokes, Fox et al. 2006) The objective was to determine whether there is an altered muscle activation pattern when using a ramped effort. This approach however does not address the issue of which discrete muscle group or groups might account for the difference between activation patterns in subjects with joint dysfunctions and those without. Furthermore, this method does not take into consideration the internal structural joint motions and thus provides an incomplete set of information upon which to draw diagnostic conclusions.

SUMMARY OF THE INVENTION

An imaging system that comprises a tracking system and an imaging system that communicate information through real-time or near real-time feedback loops and applies continuous adjustments to the imaging environment during an imaging session based upon the imported information from the tracking system. The feedback can be configurable to dynamically change to adjust the range of motion to correspond to an achieved patient motion instead of a motion of the patient movement device.

The integrated imaging system integrates a hardware and software component and incorporates a tracking system for producing precise diagnostic information and image information for the purposes of producing an optimal imaging session, and an imaging apparatus with central control unit that communicates with each component and continuously adjusts so as to produce an most favorable imaging environment.

The integrated imaging system can be adapted and configured to import information about the testing session and adapt functional imaging settings based on the imported information. Those skilled in the art will appreciate that the system described herein can be applied or incorporated into any imaging device available now and what will be available in the future.

The imaging system integrates a series of feedback loops that share information with respect to patient positioning and imaging quality and frequency. The information can be transmitted through either a direct wire-based electronic connection between the two or more components, or through a wireless connection. The information can be the type that is derived from computer programming or from operator or patient input, or from a combination of computer programmed information plus operator and/or patient input.

Methods, systems and devices register and track imaging information real-time or near real-time and provide a feedback mechanism which impacts further imaging. As a result of the feedback, patient exposure during imaging may be reduced and image capture may be enhanced.

An aspect of the disclosure is directed to a machine-readable medium that provides instructions which, when executed by a set of processors, causes the processors to provide instructions to at least one of a motion device and an imaging device comprising: receiving information from at least one of the motion device and the imaging device during an imaging session; analyzing the received information; instructing at least one of the motion device and imaging device to change the imaging environment during the imaging session. In at least some aspects, the steps of receiving, analyzing and instructing are repeated a plurality of times during the imaging session. In other aspects, the step of instructing is performed real-time or near real-time. Real-time can, for example be performed such that the analysis calculates the data quickly enough such that no data are excluded from the analysis. Additionally, real-time can be configured to received data, process it and respond within a time frame set by outside events and in such a manner so that no delay is perceived by an operator or patient. Near real-time might include, for example a momentary lag time (seconds to minutes) within an imaging session while the information is processed and instructions are generated. The instruction can change an aspect of an imaging field and/or change a movement of a motion device. Suitable imaging devices include, but are not limited to, for example an X-ray tube and image intensifier with dosage control, a magnetic resonance scanner. Additionally, a suitable motion device can be configured to further comprise a laterally moveable platform, such as a movable platform is situated on a support which lies on an upper surface of the platform base. The machine-readable medium can further comprise a processing system. In at least some aspects the motion device is adapted to communicate motion information to the imaging device during use. Moreover, continuous adjustments can be made to an imaging environment, including, for example, changes to a range of motion of the motion device is based on a selected target motion for a patient, such as a range of motion of the device is based on a gross motion of a patient.

Another aspect of the disclosure is directed to an apparatus for use in a shared computer network being able to carry real-time data streams the apparatus comprising: means for transmitting data packages to a data destination in at least one real-time or near real-time data stream over the shared computer network, wherein each of the data packets contains instructions for controlling at least one of an imaging device and a motion control device during an imaging session. Instructions can be streamed over the shared computer network a plurality of times during the imaging session. Additionally, instruction can be configured to change an aspect of an imaging field and/or movement of a motion device. Suitable imaging devices include, but are not limited to, an X-ray tube and image intensifier with dosage control and a magnetic resonance scanner. Additionally, the motion device can further comprises a laterally moveable platform, such as a movable platform is situated on a support which lies on an upper surface of the platform base. A control arm can further be provided for driving movement of a moveable platform. Moreover, a processing system can be provided. The motion device can further be adapted to communicate motion information to the imaging device during use. Furthermore continuous adjustments are made to an imaging environment. A range of motion of the motion device can further be based on a selected target motion for a patient, or on a gross motion of a patient.

Still another aspect of the disclosure is directed to a system measuring skeletal joint motion in a subject comprising: a) a motion device adapted and configured to continuously move a joint of the subject, the motion device comprising: a platform base, and a motion platform further comprising a static platform connected to an upper surface of the platform base, a movable platform connected to at least one of the static platform or an upper surface of the platform base, wherein the static platform is adjacent the movable platform wherein movement of the movable platform is achieved in operation by a motor in communication with the moveable platform; b) an imaging device in communication with the motion device adapted and configured to obtain imaging data; and c) a computing system adapted and configured to analyze the obtained imaging data to generate an instruction and then communicate the instruction to at least one of the motion device and the imaging device. Suitable imaging devices include, but are not limited to an X-ray tube and image intensifier with dosage control and a magnetic resonance scanner. Additionally, the platform can, for example, be a laterally moveable platform, such as a platform situated on a support which lies on the upper surface of the platform base. Additionally, a control arm can be provided for driving movement of the moveable platform. Moreover a processing system can be provided. The motion device can be adapted to communicate motion information to the imaging device during use. The system can also provide continuous adjustments to the imaging environment. Suitable instruction include, for example, changes an aspect of an imaging field and/or changes to a movement of a motion device. The range of motion of the motion device is based on a selected target motion for a patient. Moreover, the range of motion of the device is based on a gross motion of a patient.

Another aspect of the disclosure is directed to a method for imaging skeletal structures in vivo comprising: i) positioning a subject on a motion device adapted and configured to move a joint during a use session; ii) imaging the subject positioned on the motion device during the use session with an imaging device; iii) collecting image data; iv) analyzing the collected image data; and v) communicating an instruction based on the analyzed image data to at least one of the motion device and imaging device prior to acquiring a subsequent image. The step of communicating an instruction can, for example, include changing an aspect of an imaging field and/or changing a movement of a motion device. As will be appreciated by those skilled in the art, the step of communicating an instruction can include, for example, transmitting a new instruction which changes one or more settings, transmitting an instruction which maintains the most recent one or more settings, transmitting an instruction that repeats an earlier one or more instructions, or providing no change in instruction in current instructions. Where no change instructions are provided, the system can be adapted and configured to automatically repeat the most recent instructions after a lag of a set amount of time from providing the image data for analysis. Additionally, suitable imaging devices include, but are not limited to an X-ray tube and image intensifier with dosage control and a magnetic resonance scanner. Additionally, the motion device can further comprises a movable platform situated on a support which lies on an upper surface of a platform base. In some cases a calibration step is carried out prior to at least one of the method steps of i) to vi). Additionally, the relative motion of lumbar vertebrae L3 to L3, L3 to L4 and L4 to L5 can be tracked simultaneously or separately and/or the relative motion of lumbar vertebrae L3 to L3, L3 to L4 and L4 to L5 are tracked simultaneously or separately. Moreover, the method can be used for a diagnosis of a pseudoarthrosis in the subject, and the method comprising analyzing the relative motion of skeletal structures in the subject. An additional step can be provided for presenting an output in graphical form.

Yet another aspect of the disclosure includes a process for capturing data and controlling skeletal joint motion of a subject comprising: (a) providing an apparatus adapted and configured to selectively cause and control joint motion of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable to a second position and selectively rotatable about an axis, and a coupling member adapted and configured to connect the fixable platform to the dynamic platform or the base; (b) positioning the subject in a first position such that a first body part of the subject is at least partially positioned adjacent the static platform, and a second body part of the subject is at least partially positioned adjacent the motion platform; (c) capturing, with a medical diagnostic device, a first diagnostic data from the subject and the apparatus; (d) transmitting the first diagnostic data from the subject to a machine-readable medium; (e) analyzing the first diagnostic data; (f) generating an instructions from the analyzed first diagnostic data; (g) transmitting the instruction to the apparatus; (h) repositioning the apparatus such that the subject is placed in a second position different from the first position; and (i) capturing, with the medical diagnostic device, second diagnostic data from the subject and the apparatus in the second position. The data capturing steps of the process can further comprise using a medical diagnostic device selected from the group consisting of X-ray scanner, X-ray tube with image intensifier tube, magnetic resonance scanner, infrared camera, computed tomography scanner, ultrasound scanner, electromyography sensor unit, digital camera and camera. Moreover, steps (b) through (i) can be repeated a plurality of times during a single imaging session. Instructions can be provided that change an aspect of an imaging field and/or change a movement of a motion device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5A and 5B show side and top view block diagrams of the horizontally configured motion control device consisting of the two sub-systems and attachment mechanisms of the preferred embodiment of the horizontally configured motion control device in a "default" configuration, according to one embodiment of the present invention; FIGS. 5C-E illustrate a device from different views;

FIGS. 6A and 6B show side view block diagrams of the horizontally configured motion control device and related parts of the preferred embodiment in the "front-up" (FIG. 5A) and "front-down" (FIG. 5B) configurations suitable for use with the system disclosed;

FIGS. 8A, 8B, and 8C show side view diagrams of a vertically configured motion control device in a "default", "top out" and "top in" configurations, respectively, according to one embodiment of the present invention;

DETAILED DESCRIPTION OF THE INVENTION

An integrated imaging system that incorporates real time tracking algorithms and feedback loops for producing precise diagnostic information, and an imaging device that is adaptable in response to the integrated imaging system and feedback loops to produce an optimal imaging session.

I. Computing Systems

The systems and methods described herein rely on a variety of computer systems, networks and/or digital devices for operation. In order to fully appreciate how the system operates an understanding of suitable computing systems is useful. The systems and methods disclosed herein are enabled as a result of application via a suitable computing system.

Figure 1A:
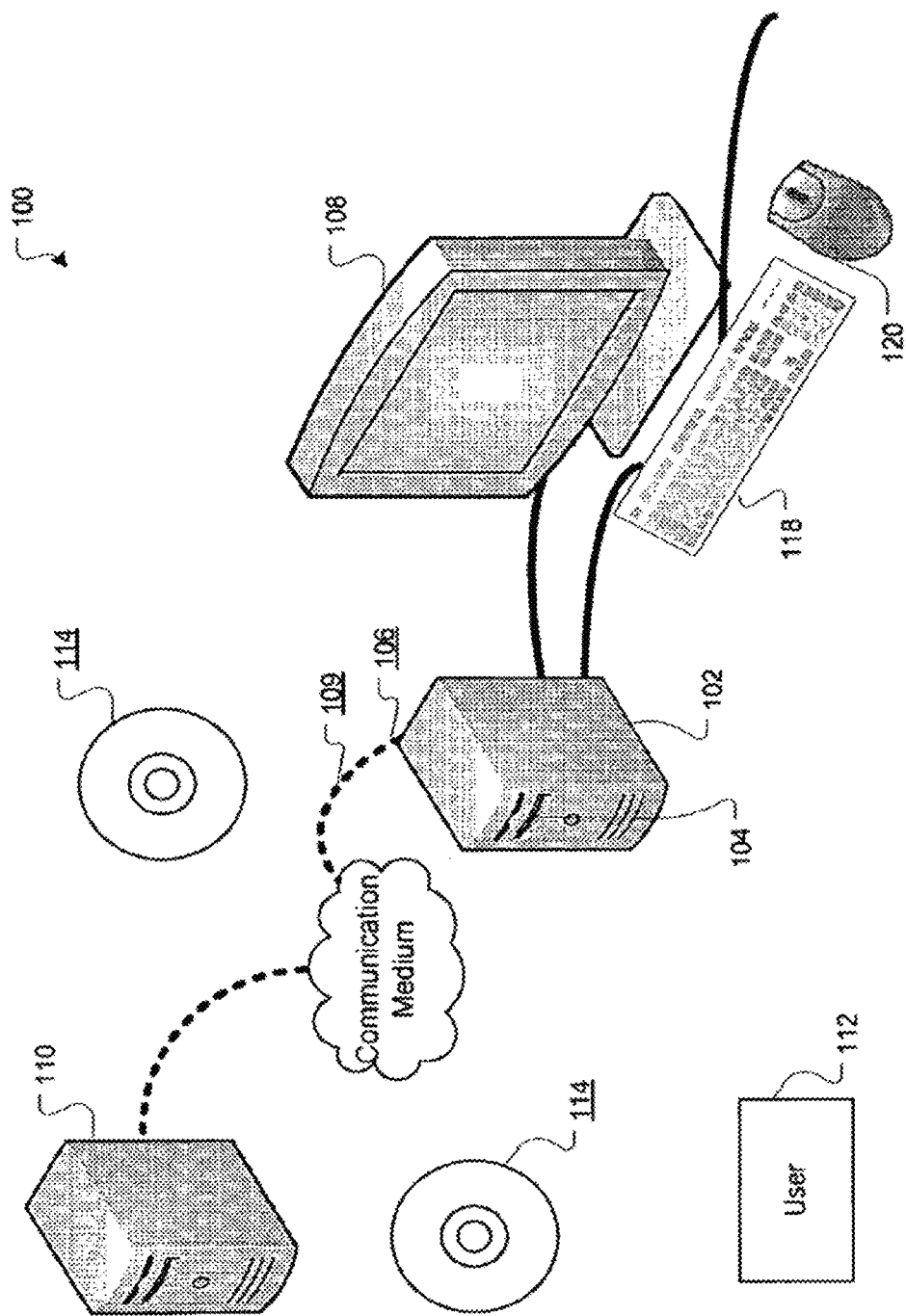
FIG. 1A is a diagram showing a representative example of a logic device through which an imaging system can provide real-time or near real-time feedback information with respect to patient position to apply adjustments to the imaging environment to optimize imaging and data acquisition.

FIG. 1A is a block diagram showing a representative example logic device through which a browser can be accessed to implement the present invention. A computer system (or digital device) 100, which may be understood as a logic apparatus adapted and configured to read instructions from media 114 and/or network port 106, is connectable to a server 110, and has a fixed media 116. The computer system 100 can also be connected to the Internet or an intranet. The system includes central processing unit (CPU) 102, disk drives 104, optional input devices, illustrated as keyboard 118 and/or mouse 120 and optional monitor 108. Data communication can be achieved through, for example, communication medium 109 to a server 110 at a local or a remote location. The communication medium 109 can include any suitable means of transmitting and/or receiving data. For example, the communication medium can be a network connection, a wireless connection or an internet connection. It is envisioned that data relating to the present invention can be transmitted over such networks or connections. The computer system can be adapted to communicate with a participant and/or a device used by a participant. The computer system is adaptable to communicate with other computers over the Internet, or with computers via a server.

Figure 1B:
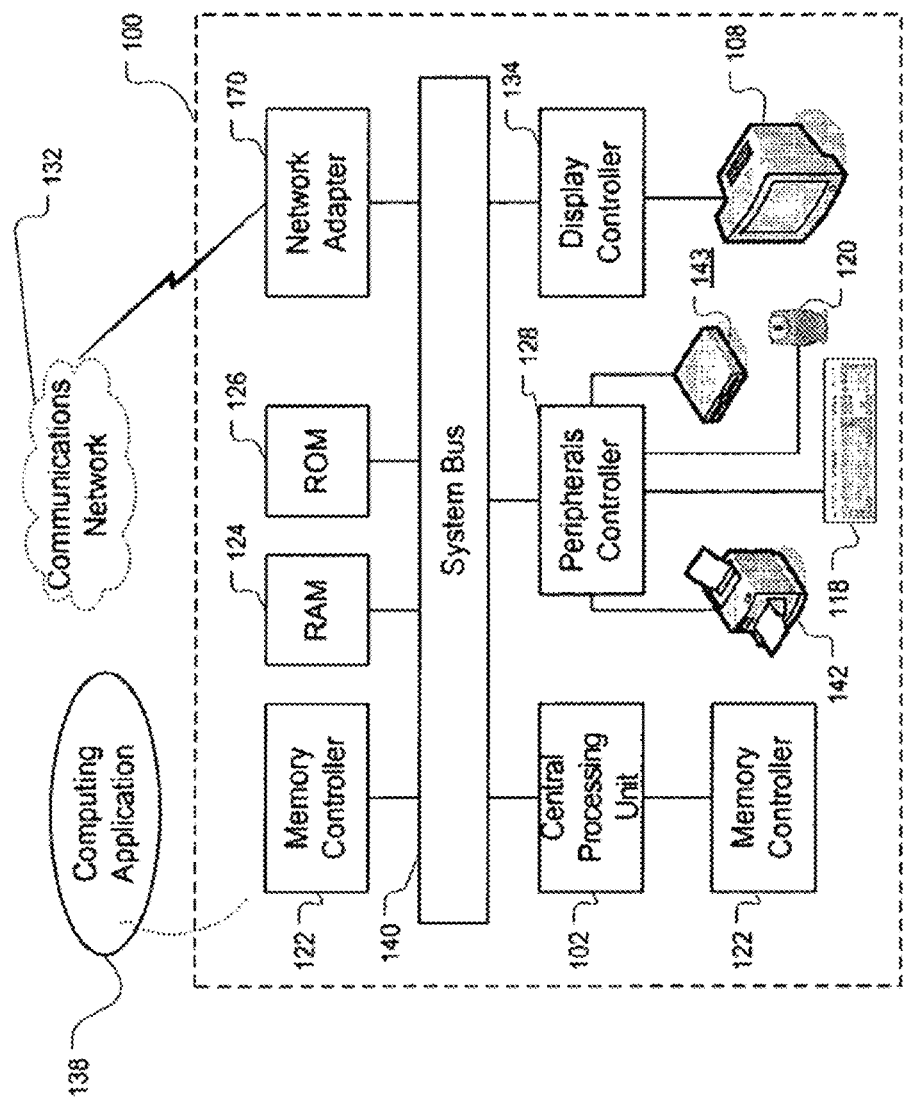
FIG. 1B is a block diagram of an exemplary computing environment through which an imaging system can provide real-time or near real-time feedback information with respect to patient position to apply adjustments to the imaging environment to optimize imaging and data acquisition.

FIG. 1B depicts another exemplary computing system 100. The computing system 100 is capable of executing a variety of computing applications 138, including computing applications, a computing applet, a computing program, or other instructions for operating on computing system 100 to perform at least one function, operation, and/or procedure. Computing system 100 is controllable by computer readable storage media for tangibly storing computer readable instructions, which may be in the form of software. The computer readable storage media adapted to tangibly store computer readable instructions can contain instructions for computing system 100 for storing and accessing the computer readable storage media to read the instructions stored thereon themselves. Such software may be executed within CPU 102 to cause the computing system 100 to perform desired functions. In many known computer servers, workstations and personal computers CPU 102 is implemented by micro-electronic chips CPUs called microprocessors. Optionally, a co-processor, distinct from the main CPU 102, can be provided that performs additional functions or assists the CPU 102. The CPU 102 may be connected to co-processor through an interconnect. One common type of coprocessor is the floating-point coprocessor, also called a numeric or math coprocessor, which is designed to perform numeric calculations faster and better than the general-purpose CPU 102.

As will be appreciated by those skilled in the art, a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor In operation, the CPU 102 fetches, decodes, and executes instructions, and transfers information to and from other resources via the computer's main data-transfer path, system bus 140. Such a system bus connects the components in the computing system 100 and defines the medium for data exchange. Memory devices coupled to the system bus 140 include random access memory (RAM) 124 and read only memory (ROM) 126. Such memories include circuitry that allows information to be stored and retrieved. The ROMs 126 generally contain stored data that cannot be modified. Data stored in the RAM 124 can be read or changed by CPU 102 or other hardware devices. Access to the RAM 124 and/or ROM 126 may be controlled by memory controller 122. The memory controller 122 may provide an address translation function that translates virtual addresses into physical addresses as instructions are executed.

In addition, the computing system 100 can contain peripherals controller 128 responsible for communicating instructions from the CPU 102 to peripherals, such as, printer 142, keyboard 118, mouse 120, and data storage drive 143. Display 108, which is controlled by a display controller 163, is used to display visual output generated by the computing system 100. Such visual output may include text, graphics, animated graphics, and video. The display controller 134 includes electronic components required to generate a video signal that is sent to display 108. Further, the computing system 100 can contain network adaptor 136 which may be used to connect the computing system 100 to an external communications network 132.

II. Networks and Internet Protocol

As is well understood by those skilled in the art, the Internet is a worldwide network of computer networks. Today, the Internet is a public and self-sustaining network that is available to many millions of users. The Internet uses a set of communication protocols called TCP/IP (i.e., Transmission Control Protocol/Internet Protocol) to connect hosts. The Internet has a communications infrastructure known as the Internet backbone. Access to the Internet backbone is largely controlled by Internet Service Providers (ISPs) that resell access to corporations and individuals.

The Internet Protocol (IP) enables data to be sent from one device (e.g., a phone, a Personal Digital Assistant (PDA), a computer, etc.) to another device on a network. There are a variety of versions of IP today, including, e.g., IPv4, IPv6, etc. Other IPs are no doubt available and will continue to become available in the future, any of which can be used without departing from the scope of the invention. Each host device on the network has at least one IP address that is its own unique identifier and acts as a connectionless protocol. The connection between end points during a communication is not continuous. When a user sends or receives data or messages, the data or messages are divided into components known as packets. Every packet is treated as an independent unit of data and routed to its final destination—but not necessarily via the same path.

The Open System Interconnection (OSI) model was established to standardize transmission between points over the Internet or other networks. The OSI model separates the communications processes between two points in a network into seven stacked layers, with each layer adding its own set of functions. Each device handles a message so that there is a downward flow through each layer at a sending end point and an upward flow through the layers at a receiving end point. The programming and/or hardware that provides the seven layers of function is typically a combination of device operating systems, application software, TCP/IP and/or other transport and network protocols, and other software and hardware.

Typically, the top four layers are used when a message passes from or to a user and the bottom three layers are used when a message passes through a device (e.g., an IP host device). An IP host is any device on the network that is capable of transmitting and receiving IP packets, such as a server, a router or a workstation. Messages destined for some other host are not passed up to the upper layers but are forwarded to the other host. The layers of the OSI model are listed below. Layer 7 (i.e., the application layer) is a layer at which, e.g., communication partners are identified, quality of service is identified, user authentication and privacy are considered, constraints on data syntax are identified, etc. Layer 6 (i.e., the presentation layer) is a layer that, e.g., converts incoming and outgoing data from one presentation format to another, etc. Layer 5 (i.e., the session layer) is a layer that, e.g., sets up, coordinates, and terminates conversations, exchanges and dialogs between the applications, etc. Layer-4 (i.e., the transport layer) is a layer that, e.g., manages end-to-end control and error-checking, etc. Layer-3 (i.e., the network layer) is a layer that, e.g., handles routing and forwarding, etc. Layer-2 (i.e., the data-link layer) is a layer that, e.g., provides synchronization for the physical level, does bit-stuffing and furnishes transmission protocol knowledge and management, etc. The Institute of Electrical and Electronics Engineers (IEEE) sub-divides the data-link layer into two further sub-layers, the MAC (Media Access Control) layer that controls the data transfer to and from the physical layer and the LLC (Logical Link Control) layer that interfaces with the network layer and interprets commands and performs error recovery. Layer 1 (i.e., the physical layer) is a layer that, e.g., conveys the bit stream through the network at the physical level. The IEEE sub-divides the physical layer into the PLCP (Physical Layer Convergence Procedure) sub-layer and the PMD (Physical Medium Dependent) sub-layer.

III. Wireless Networks

Wireless networks can incorporate a variety of types of mobile devices, such as, e.g., cellular and wireless telephones, PCs (personal computers), laptop computers, wearable computers, cordless phones, pagers, headsets, printers, PDAs, etc. For example, mobile devices may include digital systems to secure fast wireless transmissions of voice and/or data. Typical mobile devices include some or all of the following components: a transceiver (for example a transmitter and a receiver, including a single chip transceiver with an integrated transmitter, receiver and, if desired, other functions); an antenna; a processor; display; one or more audio transducers (for example, a speaker or a microphone as in devices for audio communications); electromagnetic data storage (such as ROM, RAM, digital data storage, etc., such as in devices where data processing is provided); memory; flash memory; and/or a full chip set or integrated circuit; interfaces (such as universal serial bus (USB), coder-decoder (CODEC), universal asynchronous receiver-transmitter (UART), phase-change memory (PCM), etc.). Other components can be provided without departing from the scope of the invention.

Wireless LANs (WLANs) in which a mobile user can connect to a local area network (LAN) through a wireless connection may be employed for wireless communications. Wireless communications can include communications that propagate via electromagnetic waves, such as light, infrared, radio, and microwave. There are a variety of WLAN standards that currently exist, such as Bluetooth®, IEEE 802.11, and the obsolete HomeRF.

By way of example, Bluetooth products may be used to provide links between mobile computers, mobile phones, portable handheld devices, personal digital assistants (PDAs), and other mobile devices and connectivity to the Internet. Bluetooth is a computing and telecommunications industry specification that details how mobile devices can easily interconnect with each other and with non-mobile devices using a short-range wireless connection. Bluetooth creates a digital wireless protocol to address end-user problems arising from the proliferation of various mobile devices that need to keep data synchronized and consistent from one device to another, thereby allowing equipment from different vendors to work seamlessly together.

An IEEE standard, IEEE 802.11, specifies technologies for wireless LANs and devices. Using 802.11, wireless networking may be accomplished with each single base station supporting several devices. In some examples, devices may come pre-equipped with wireless hardware or a user may install a separate piece of hardware, such as a card, that may include an antenna. By way of example, devices used in 802.11 typically include three notable elements, whether or not the device is an access point (AP), a mobile station (STA), a bridge, a personal computing memory card International Association (PCMCIA) card (or PC card) or another device: a radio transceiver; an antenna; and a MAC (Media Access Control) layer that controls packet flow between points in a network.

In addition, Multiple Interface Devices (MIDs) may be utilized in some wireless networks. MIDs may contain two independent network interfaces, such as a Bluetooth interface and an 802.11 interface, thus allowing the MID to participate on two separate networks as well as to interface with Bluetooth devices. The MID may have an IP address and a common IP (network) name associated with the IP address.

Wireless network devices may include, but are not limited to Bluetooth devices, WiMAX (Worldwide Interoperability for Microwave Access), Multiple Interface Devices (MIDs), 802.11x devices (IEEE 802.11 devices including, 802.11a, 802.11b and 802.11g devices), HomeRF (Home Radio Frequency) devices, Wi-Fi (Wireless Fidelity) devices, GPRS (General Packet Radio Service) devices, 3 G cellular devices, 2.5 G cellular devices, GSM (Global System for Mobile Communications) devices, EDGE (Enhanced Data for GSM Evolution) devices, TDMA type (Time Division Multiple Access) devices, or CDMA type (Code Division Multiple Access) devices, including CDMA2000. Each network device may contain addresses of varying types including but not limited to an IP address, a Bluetooth Device Address, a Bluetooth Common Name, a Bluetooth IP address, a Bluetooth IP Common Name, an 802.11 IP Address, an 802.11 IP common Name, or an IEEE MAC address.

Wireless networks can also involve methods and protocols found in, Mobile IP (Internet Protocol) systems, in PCS systems, and in other mobile network systems. With respect to Mobile IP, this involves a standard communications protocol created by the Internet Engineering Task Force (IETF). With Mobile IP, mobile device users can move across networks while maintaining their IP Address assigned once. See Request for Comments (RFC) 3344. NB: RFCs are formal documents of the Internet Engineering Task Force (IETF). Mobile IP enhances Internet Protocol (IP) and adds a mechanism to forward Internet traffic to mobile devices when connecting outside their home network. Mobile IP assigns each mobile node a home address on its home network and a care-of-address (CoA) that identifies the current location of the device within a network and its subnets. When a device is moved to a different network, it receives a new care-of address. A mobility agent on the home network can associate each home address with its care-of address. The mobile node can send the home agent a binding update each time it changes its care-of address using Internet Control Message Protocol (ICMP).

In basic IP routing (e.g., outside mobile IP), routing mechanisms rely on the assumptions that each network node always has a constant attachment point to the Internet and that each node's IP address identifies the network link it is attached to. In this document, the terminology "node" includes a connection point, which can include a redistribution point or an end point for data transmissions, and which can recognize, process and/or forward communications to other nodes. For example, Internet routers can look at an IP address prefix or the like identifying a device's network. Then, at a network level, routers can look at a set of bits identifying a particular subnet. Then, at a subnet level, routers can look at a set of bits identifying a particular device. With typical mobile IP communications, if a user disconnects a mobile device from the Internet and tries to reconnect it at a new subnet, then the device has to be reconfigured with a new IP address, a proper netmask and a default router. Otherwise, routing protocols would not be able to deliver the packets properly.

Figure 1C:
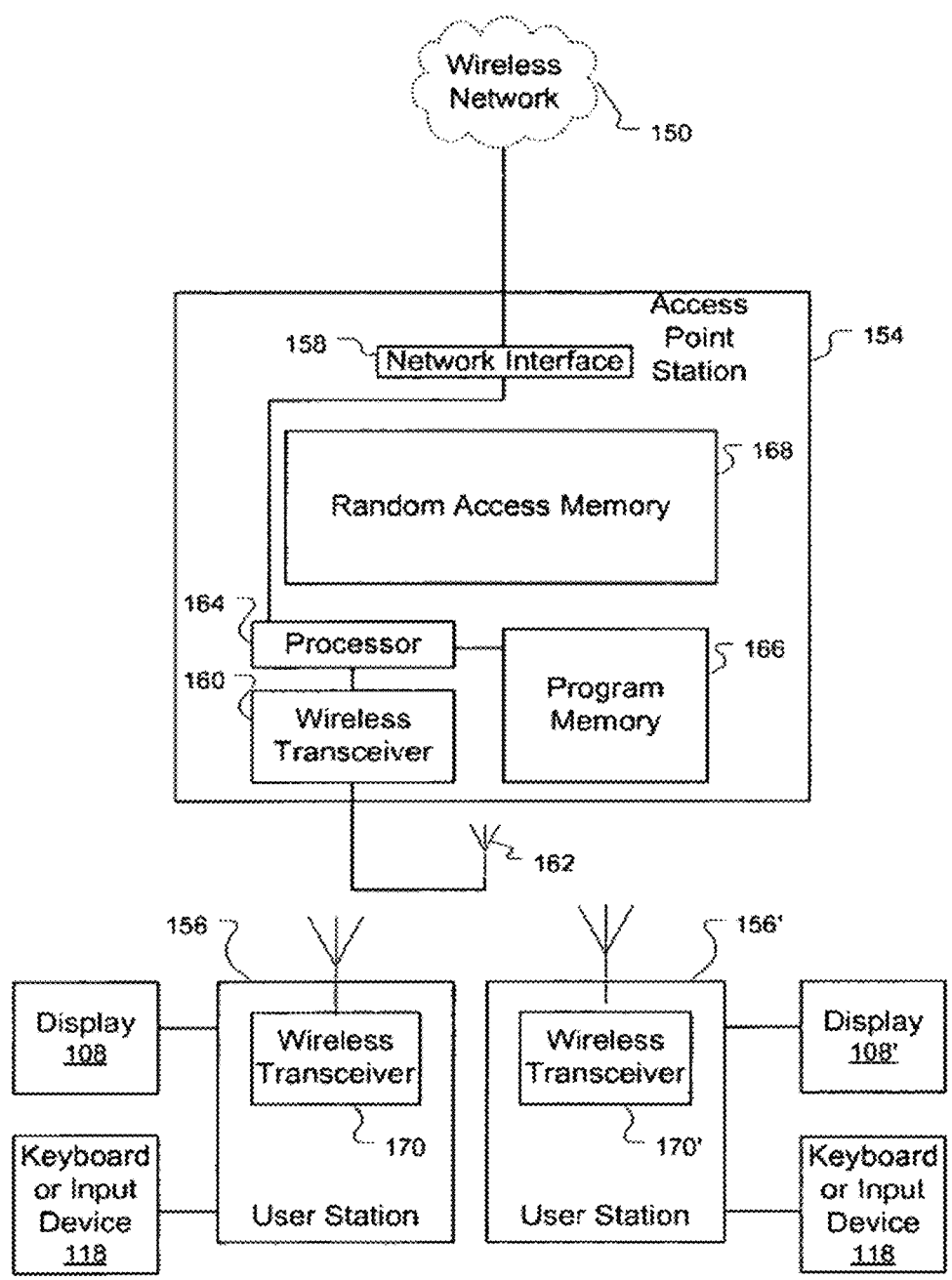
FIG. 1C is an illustrative architectural diagram showing some structure that can be employed by devices through which an imaging system can provide real-time or near real-time feedback information with respect to patient position to apply adjustments to the imaging environment to optimize imaging and data acquisition.

FIG. 1C depicts components that can be employed in system configurations enabling the systems and technical effect of this invention, including wireless access points to which client devices communicate. In this regard, FIG. 1C shows a wireless network 150 connected to a wireless local area network (WLAN) 152. The WLAN 152 includes an access point (AP) 154 and a number of user stations 156, 156'. For example, the network 150 can include the Internet or a corporate data processing network. The access point 154 can be a wireless router, and the user stations 156, 156' can be portable computers, personal desk-top computers, PDAs, portable voice-over-IP telephones and/or other devices. The access point 154 has a network interface 158 linked to the network 150, and a wireless transceiver in communication with the user stations 156, 156'. For example, the wireless transceiver 160 can include an antenna 162 for radio or microwave frequency communication with the user stations 156, 156'. The access point 154 also has a processor 164, a program memory 166, and a random access memory 168. The user station 156 has a wireless transceiver 170 including an antenna 172 for communication with the access point station 154. In a similar fashion, the user station 156' has a wireless transceiver 170' and an antenna 172' for communication to the access point 154. By way of example, in some embodiments an authenticator could be employed within such an access point (AP) and/or a supplicant or peer could be employed within a mobile node or user station. Desktop 108 and keyboard 118 or input devices can also be provided with the user status.

IV. Media Independent Handover Services

In IEEE P802.21/D.01.09, September 2006, entitled Draft IEEE Standard for Local and Metropolitan Area Networks: Media Independent Handover Services, among other things, the document specifies 802 media access-independent mechanisms that optimize handovers between 802 systems and cellular systems. The IEEE 802.21 standard defines extensible media access independent mechanisms that enable the optimization of handovers between heterogeneous 802 systems and may facilitate handovers between 802 systems and cellular systems. "The scope of the IEEE 802.21 (Media Independent Handover) standard is to develop a specification that provides link layer intelligence and other related network information to upper layers to optimize handovers between heterogeneous media. This includes links specified by 3GPP, 3GPP2 and both wired and wireless media in the IEEE 802 family of standards. Note, in this document, unless otherwise noted, "media" refers to method/mode of accessing a telecommunication system (e.g. cable, radio, satellite, etc.), as opposed to sensory aspects of communication (e.g. audio, video, etc.)." See 1.1 of I.E.E.E. P802.21/D.01.09, September 2006, entitled Draft IEEE Standard for Local and Metropolitan Area Networks: Media Independent Handover Services, the entire contents of which document is incorporated herein into and as part of this patent application. Other IEEE, or other such standards on protocols can be relied on as appropriate or desirable.

Figure 2:
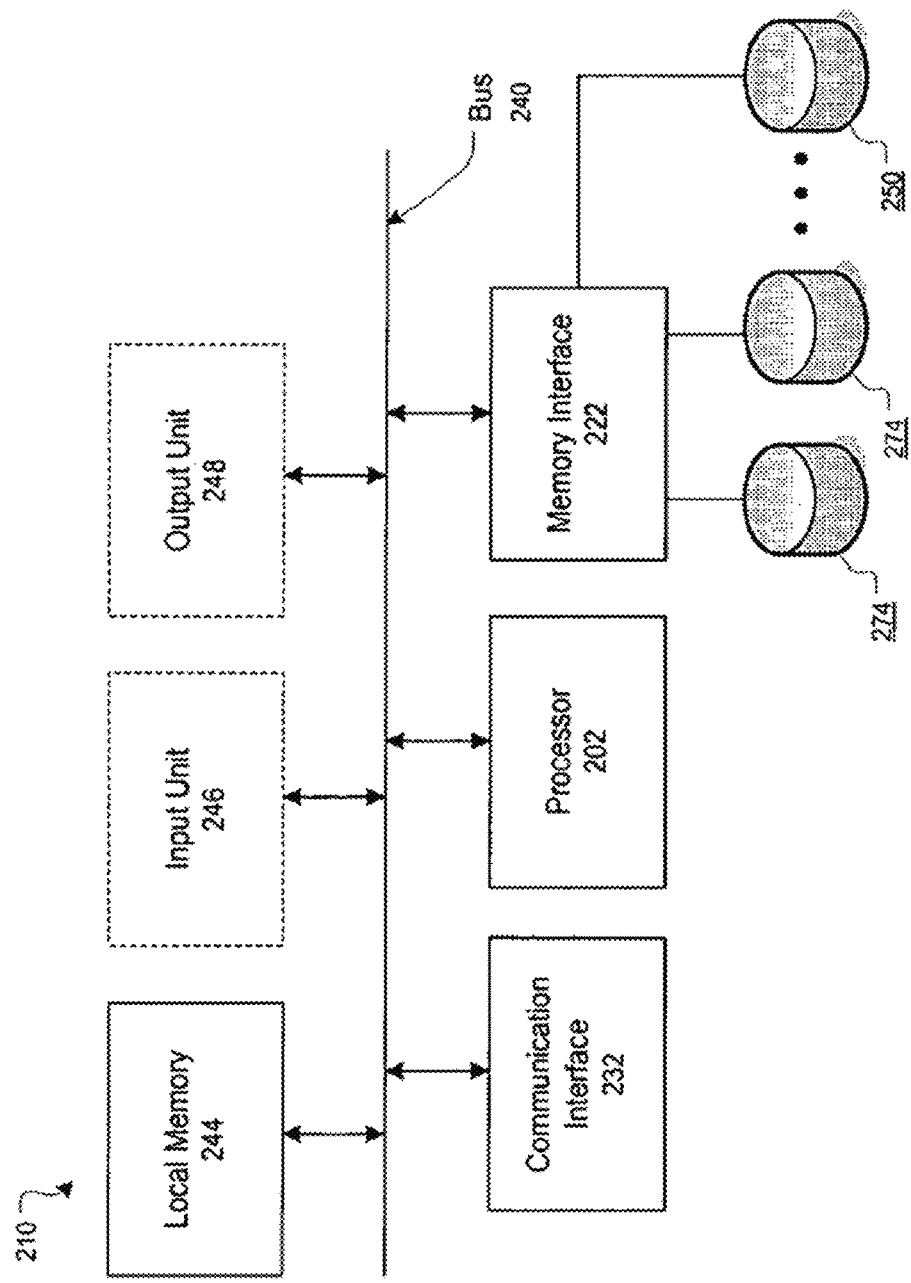
FIG. 2 is an exemplary diagram of a server in an implementation suitable for use in a system where an imaging system can provide real-time or near real-time feedback information with respect to patient position to apply adjustments to the imaging environment to optimize imaging and data acquisition.

FIG. 2 is an exemplary diagram of a server 210 in an implementation consistent with the principles of the disclosure to achieve the desired technical effect and transformation. Server 210 may include a bus 240, a processor 202, a local memory 244, one or more optional input units 246, one or more optional output units 248, a communication interface 232, and a memory interface 222. Bus 240 may include one or more conductors that permit communication among the components of chunk server 250.

Processor 202 may include any type of conventional processor or microprocessor that interprets and executes instructions. Local memory 244 may include a random access memory (RAM) or another type of dynamic storage device that stores information and instructions for execution by processor 202 and/or a read only memory (ROM) or another type of static storage device that stores static information and instructions for use by processor 202.

Input unit 246 may include one or more conventional mechanisms that permit an operator to input information to a server 110, such as a keyboard 118, a mouse 120 (shown in FIG. 1), a pen, voice recognition and/or biometric mechanisms, etc. Output unit 248 may include one or more conventional mechanisms that output information to the operator, such as a display 134, a printer 130 (shown in FIG. 1), a speaker, etc. Communication interface 232 may include any transceiver-like mechanism that enables chunk server 250 to communicate with other devices and/or systems. For example, communication interface 232 may include mechanisms for communicating with master and clients.

Memory interface 222 may include a memory controller 122. Memory interface 222 may connect to one or more memory devices, such as one or more local disks 274, and control the reading and writing of chunk data to/from local disks 276. Memory interface 222 may access chunk data using a chunk handle and a byte range within that chunk.

Figure 3:
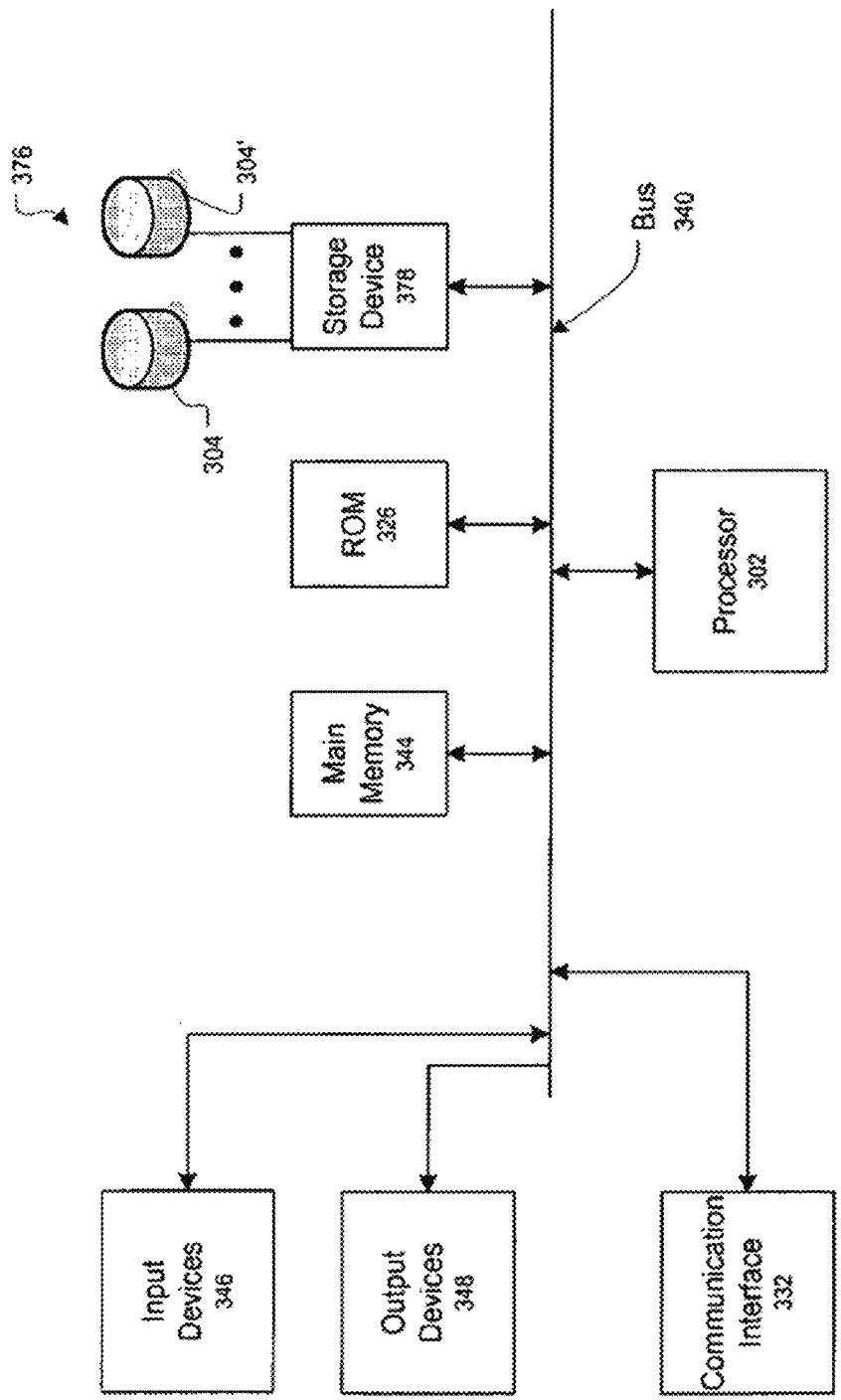
FIG. 3 is an exemplary diagram of a master system in an implementation suitable for use in a system where an imaging system can provide real-time or near real-time feedback information with respect to patient position to apply adjustments to the imaging environment to optimize imaging and data acquisition.

FIG. 3 is an exemplary diagram of a master system 376 suitable for use in an implementation consistent with the principles of the disclosure to achieve the desired technical effect and transformation. Master system 376 may include a bus 340, a processor 302, a main memory 344, a ROM 326, a storage device 378, one or more input devices 346, one or more output devices 348, and a communication interface 332. Bus 340 may include one or more conductors that permit communication among the components of master system 374.

Processor 302 may include any type of conventional processor or microprocessor that interprets and executes instructions. Main memory 344 may include a RAM or another type of dynamic storage device that stores information and instructions for execution by processor 302. ROM 326 may include a conventional ROM device or another type of static storage device that stores static information and instructions for use by processor 302. Storage device 378 may include a magnetic and/or optical recording medium and its corresponding drive. For example, storage device 378 may include one or more local disks that provide persistent storage.

Input devices 346 used to achieve the desired technical effect and transformation may include one or more conventional mechanisms that permit an operator to input information to the master system 374, such as a keyboard 118, a mouse 120, (shown in FIG. 1) a pen, voice recognition and/or biometric mechanisms, etc. Output devices 348 may include one or more conventional mechanisms that output information to the operator, including a display 108, a printer 142 (shown in FIG. 1), a speaker, etc. Communication interface 332 may include any transceiver-like mechanism that enables master system 374 to communicate with other devices and/or systems. For example, communication interface 332 may include mechanisms for communicating with servers and clients as shown above.

Master system 376 used to achieve the desired technical effect and transformation may maintain file system metadata within one or more computer readable mediums, such as main memory 344 and/or storage device.

The computer implemented system provides a storage and delivery base which allows users to exchange services and information openly on the Internet used to achieve the desired technical effect and transformation. A user will be enabled to operate as both a consumer and producer of any and all digital content or information through one or more master system servers.

A user executes a browser to view digital content items and can connect to the front end server via a network, which is typically the Internet, but can also be any network, including but not limited to any combination of a LAN, a MAN, a WAN, a mobile, wired or wireless network, a private network, or a virtual private network. As will be understood a very large numbers (e.g., millions) of users are supported and can be in communication with the website at any time. The user may include a variety of different computing devices. Examples of user devices include, but are not limited to, personal computers, digital assistants, personal digital assistants, cellular phones, mobile phones, smart phones or laptop computers.

The browser can include any application that allows users to access web pages on the World Wide Web. Suitable applications include, but are not limited to, Microsoft Internet Explorer®, Netscape Navigator®, Mozilla® Firefox, Apple® Safari or any application adapted to allow access to web pages on the World Wide Web. The browser can also include a video player (e.g., Flash™ from Adobe Systems, Inc.), or any other player adapted for the video file formats used in the video hosting website. Alternatively, videos can be accessed by a standalone program separate from the browser. A user can access a video from the website by, for example, browsing a catalog of digital content, conducting searches on keywords, reviewing aggregate lists from other users or the system administrator (e.g., collections of videos forming channels), or viewing digital content associated with particular user groups (e.g., communities).

V. Computer Network Environment

Figure 4:
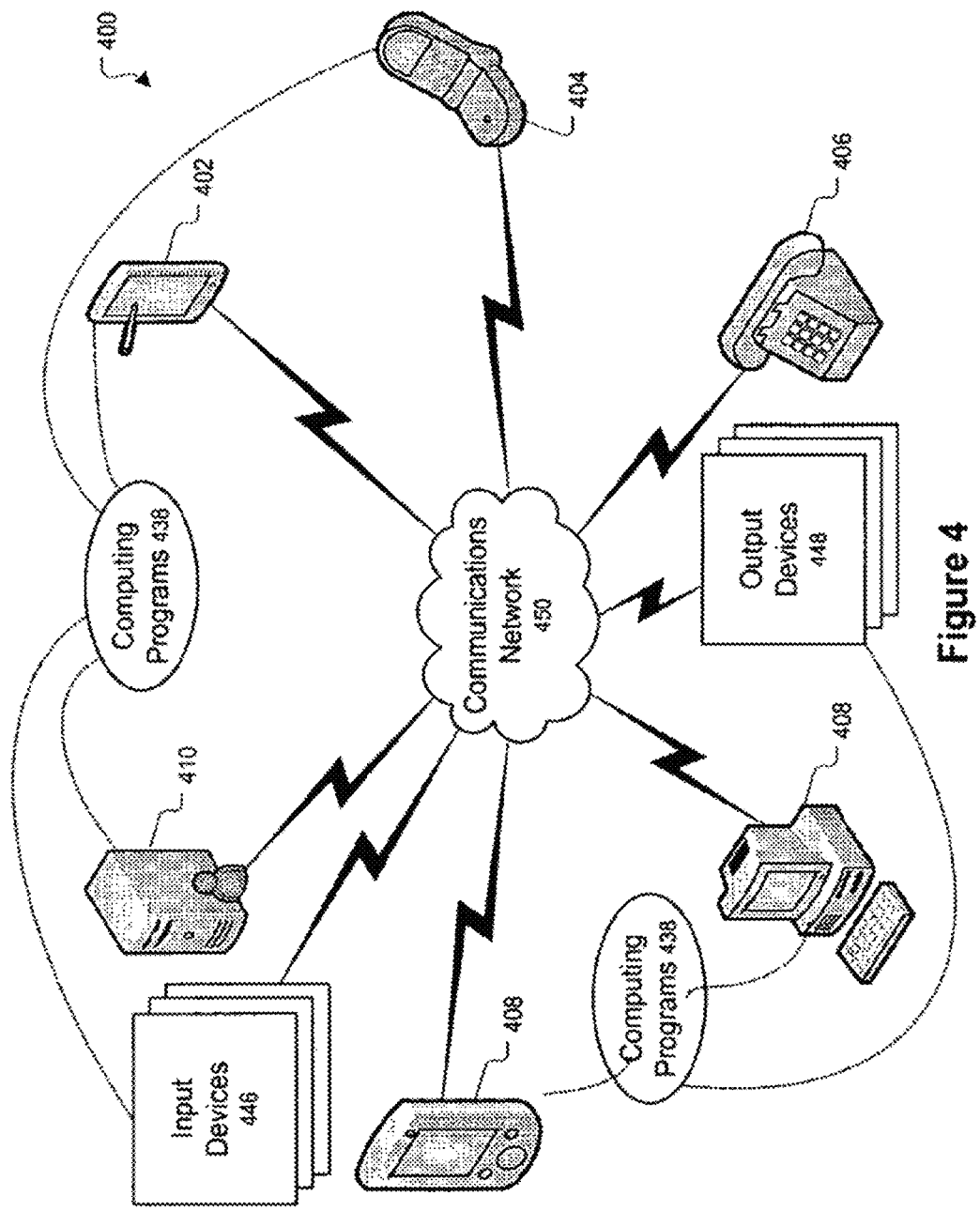
FIG. 4 is a block diagram showing the cooperation of exemplary components of a system suitable for use in a system where an imaging system can provide real-time or near real-time feedback information with respect to patient position to apply adjustments to the imaging environment to optimize imaging and data acquisition.

Computing system 100, described above, can be deployed as part of a computer network used to achieve the desired technical effect and transformation. In general, the above description for computing environments applies to both server computers and client computers deployed in a network environment. FIG. 4 illustrates an exemplary illustrative networked computing environment 400, with a server in communication with client computers via a communications network 450. As shown in FIG. 4, server 410 may be interconnected via a communications network 450 (which may be either of, or a combination of a fixed-wire or wireless LAN, WAN, intranet, extranet, peer-to-peer network, virtual private network, the Internet, or other communications network) with a number of client computing environments such as tablet personal computer 402, mobile telephone 404, telephone 406, personal computer 402, and personal digital assistant 408. In a network environment in which the communications network 450 is the Internet, for example, server 410 can be dedicated computing environment servers operable to process and communicate data to and from client computing environments via any of a number of known protocols, such as, hypertext transfer protocol (HTTP), file transfer protocol (FTP), simple object access protocol (SOAP), or wireless application protocol (WAP). Other wireless protocols can be used without departing from the scope of the disclosure, including, for example Wireless Markup Language (WML), DoCoMo i-mode (used, for example, in Japan) and XHTML Basic. Additionally, networked computing environment 400 can utilize various data security protocols such as secured socket layer (SSL) or pretty good privacy (PGP). Each client computing environment can be equipped with operating system 438 operable to support one or more computing applications, such as a web browser (not shown), or other graphical user interface (not shown), or a mobile desktop environment (not shown) to gain access to server computing environment 400.

In operation, a user (not shown) may interact with a computing application running on a client computing environment to obtain desired data and/or computing applications. The data and/or computing applications may be stored on server computing environment 400 and communicated to cooperating users through client computing environments over exemplary communications network 450. The computing applications, described in more detail below, are used to achieve the desired technical effect and transformation set forth. A participating user may request access to specific data and applications housed in whole or in part on server computing environment 400. These data may be communicated between client computing environments and server computing environments for processing and storage. Server computing environment 400 may host computing applications, processes and applets for the generation, authentication, encryption, and communication data and applications and may cooperate with other server computing environments (not shown), third party service providers (not shown), network attached storage (NAS) and storage area networks (SAN) to realize application/data transactions.

The communication network is adaptable and configurable to be in communication with one or more input devices 446 and/or one or more output devices 448 as discussed above. In general input devices are those devices or components that provide information to the system and output devices are those devices or components that provide information from the system. As will be appreciated by those skilled in the device a single device can, at times, be capable of operating as both an input device and an output device. For purposes of appreciating the context of the disclosure, suitable input devices are, for example, those devices that input information into the system such as imaging devices and/or patient motion control devices as discussed herein. Suitable output devices are, for example, those devices that receive information and/or data from one or more input devices, in a computing environment (such as shown in FIG. 4), process the received information and/or data, and generate a return real-time or near real-time signal to the input devices to achieve a technical effect of controlling the behavior or performance of the input devices to achieve a desired VI. Media Independent Information Service The Media Independent Information Service (MIIS) provides a framework and corresponding mechanisms by which an MIHF entity may discover and obtain network information existing within a geographical area to facilitate handovers. Additionally or alternatively, neighboring network information discovered and obtained by this framework and mechanisms can also be used in conjunction with user and network operator policies for optimum initial network selection and access (attachment), or network re-selection in idle mode.

MIIS primarily provides a set of information elements (IEs), the information structure and its representation, and a query/response type of mechanism for information transfer.

The information can be present in some information server from which, e.g., an MIHF in the Mobile Node (MN) can access it.

Depending on the type of mobility, support for different types of information elements may be necessary for performing handovers. MIIS provides the capability for obtaining information about lower layers such as neighbor maps and other link layer parameters, as well as information about available higher layer services such as Internet connectivity.

MIIS provides a generic mechanism to allow a service provider and a mobile user to exchange information on different handover candidate access networks. The handover candidate information can include different access technologies such as IEEE 802 networks, 3GPP networks and 3GPP2 networks. The MIIS also allows this collective information to be accessed from any single network. For example, by using an IEEE 802.11 access network, it can be possible to get information not only about all other IEEE 802 based networks in a particular region but also about 3GPP and 3GPP2 networks. Similarly, using, e.g., a 3GPP2 interface, it can be possible to get access to information about all IEEE 802 and 3GPP networks in a given region. This capability allows the MN to use its currently active access network and inquire about other available access networks in a geographical region. Thus, a MN is freed from the burden of powering up each of its individual radios and establishing network connectivity for the purpose of retrieving heterogeneous network information. MIIS enables this functionality across all available access networks by providing a uniform way to retrieve heterogeneous network information in any geographical area.

VII. Devices

Motion control device can be is represented by a large box that contains various subsystems. Suitable motion control devices can either be passive or active. As will be appreciated by those of skill in the art, the motion control device, can also be a horizontally configured motion control device, a vertically configured motion control device or a butterfly configured device. Motion control devices suitable for use with the systems include any of the motion control devices described herein as well as any other device suitable for controlling the motion of a target patient anatomy.

The diagnostic imaging hardware contains a field of imaging, which is a physical space in which objects imaged by the hardware must be located during the imaging process to produce images. The field of imaging can contain a posture assistance device such as a table, bed, chair, or other device intended to bear all or some of the subject's weight and to provide physical support to a specific type of posture. Alternatively, the field of imaging can contain no such devices if the subject can be situated directly onto the floor and/or the motion control device and does not require the use of an additional device to bear weight and/or support specific postures, according to one embodiment of the present invention. The motion control device, or sub-systems therein, occupy part or the entire field of imaging and is physically connected and supported either by resting on the floor itself, or by being physically and immovably attached to the imaging equipment or a posture-assistance devices within the field of imaging. All parts of the horizontally configured motion control device that are located within the field of imaging are constructed of materials that are either radiolucent in the case of use with videoflouroscopic and moving CT imaging systems, or alternatively compatible with MRI images in the case of a moving MRI imaging system, and therefore these parts of the motion control device do not obscure or produce artifacts on the diagnostic images. The motion control device may also have the capacity to have pillows, cushions, and/or restraining devices attached to it at points where these pillows, cushions, and/or restraining devices aid in improving the comfort of the subject and/or in producing the correct posture and/or motion required for the test. The motion control device as a unit is attachable and detachable by the operator within the field of imaging, according to one embodiment of the present invention.

A base is provided for the purpose of physically and immovably fixing and stabilizing the motion control device within the field of imaging to either the floor, the imaging equipment, and/or a posture-assistance device while the images and other measurements are being collected, and also for the purpose of providing an immoveable fixed structure on which to attach other sub-systems of the motion control device. The base connects via attachment mechanisms at the points of contact between the base and either the floor, the imaging equipment, and/or a posture-assistance device.

As the motion control device physically attaches to and therefore may bear its weight onto the base, and as the motion control device can be configured to also bear the entire weight of the subject, and with the subject moving during the testing process and therefore producing both static and dynamic forces, the base needs the structural integrity and gripping force required to remain static, stable, and fixed in the presence of such loads and forces. The structural integrity is afforded by the use of rigid and strong materials such as plastics when radiolucent materials are desirable and in situations where compatibility with dynamic MRI systems is required, according to one embodiment of the present invention. Said gripping force is afforded by the use of strong fixation mechanisms at the points of contact, and may be accomplished by either: (1) the weight of the motion control device itself, and the friction caused thereby and enhanced by the use of high-friction materials such as rubber at the points of contact, to fix and stabilize the motion control device; (2) screws, clamps, bolts, fasteners, straps, ties, cuffs, nuts, pins, or any other rigid or flexible fixation mechanism that provides immoveable fixation at the points of contact; and/or (3) some combination therein.

Base can be a highly configurable sub-system, adapted and configured to have several configurations and versions to accommodate the different types of postures; different types, sizes, and configurations of posture-assistance devices; different sizes and geometries of imaging equipment and imaging fields; different materials at the point of contact to which to connect between the base and either the floor, the imaging equipment, and/or a posture-assistance device; and different geometries and sizes of these points of contact.

As applied to a butterfly motion control device, the diagnostic imaging hardware contains a field of imaging, which is a physical space in which objects imaged by the hardware must be located during the imaging process to produce images. The field of imaging can contain a posture assistance device such as a table, bed, chair, or other device intended to bear all or some of the subject's weight and to provide physical support to a specific type of posture. Alternatively, the field of imaging can contain no such devices if the subject can be situated directly onto the floor and/or the motion control device and does not require the use of an additional device to bear weight and/or support specific postures. The "butterfly" motion control device, or sub-systems therein, occupy part or the entire field of imaging and is physically connected and supported either by resting on the floor itself, or by being physically and immovably attached to the imaging equipment or to one of the above-mentioned posture-assistance devices within the field of imaging. All parts of the "butterfly" motion control device that are located within the field of imaging are constructed of materials that are either radiolucent in the case of use with videoflouroscopic and moving CT imaging systems, or alternatively compatible with on MRI images in the case of a moving MRI imaging system, and therefore these parts of the "butterfly" motion control device do not obscure or produce artifacts on the diagnostic images. The "butterfly" motion control device also has the capacity to have pillows, cushions, and/or restraining devices attached to it at points where these pillows, cushions, and/or restraining devices aid in improving the comfort of the subject and/or in producing the correct posture and/or motion required for the test. The "butterfly" motion control device is attachable and detachable by the operator within the field of imaging. As will be appreciated by those skilled in the art, other devices adapted and configured to control movement of a target patient anatomy can be used without departing from the scope of the disclosure.

Turning now to FIGS. 5A and 5B, an illustration of a configuration of a horizontally configured motion control device 25 is provided for purposes of illustration. The base 31 serves as the base for the horizontally configured motion control device 25. The device 25 can be adapted and configured such that all other sub-systems attach or engage the base in some way. The base 31 can be optionally adapted and configured to detachably attach to either the floor, the imaging equipment, and/or a posture-assistance device 53 via the detachable anchoring device 55. The operator can then remove the motion control device 25 from the field of imaging. Moving up from this base 31, the next two physical sub-systems are the static platform 33 and the motion platform 35. The static platform 33 and the motion platform 35 are attached to each other by a suitable mechanism such as a hinging mechanism 73. When the device is in the "default" position, shown in FIGS. 5A and 5B, the device is locked such that the flat surfaces of both the motion platform 35 and static platform 33 reside within the same plane, but that still allows for the free rotation of the motion platform 35 within a plane (e.g., plane a-c) of its subject-facing surface about a fixed axis (b) of rotation. Other configurations or embodiments are possible that afford for the horizontal motion platform to move in a plane that is at an angle to the horizontal static platform. These "non-default" configurations are described in detail later in subsequent drawings.

The static platform 33 and motion platform 35 attach to the base 31 differently. See FIGS. 5A and 5B for a graphical description of how these sub-systems can be adapted to attach to each other. In this device, the base 31 attaches to either the floor, imaging equipment, and/or posture assistance devices 53 via the detachable anchoring device 55 and also connects to the static platform 33, which is held firm by a rigid immobilized static platform/member attachment mechanism 49. The base 31 and the motion platform 35 are attached by way of the motion platform attachment mechanism 51 that along with the hinging mechanism 73 allows for free rotation of the motion platform 35 within the plane of its flat subject-facing surface, while simultaneously allowing for the adjustment of the angle that this plane makes with the subject-facing surface of the static platform 33, such that these two planes intersect along the line of the hinge which occupies the linear space defined by the edges of these two platforms that face and are adjacent to each other. In the "default" configuration represented in FIGS. 5A and 5B, this angle is set to 180 degrees. In other "non-default" configurations, this angle can be adjusted to angles other than 180 degrees. The radio-opaque protractor 74 is shown on FIG. 5A. FIGS. 5C-E illustrate a configuration of a suitable device.

FIGS. 6A and 6B illustrate the functionality of the motion platform attachment mechanism 51 and the hinging mechanism 73. FIG. 6A depicts the side view block diagram of attachment mechanisms and parts of the horizontally configured motion control device 25 in a "front up" configuration, where the hinging mechanism 73 connects the static platform 33 with the motion platform 35 along the edges of these platforms that face each other in such a way as to allow these two platforms to rotate about an axis c of the hinge. In this configuration, the connection between the base 31 and the static platform 33 is held firm by the rigid immobilized static platform/member attachment mechanism 49. However, the motion platform attachment mechanism 51 between the base 31 and the motion platform 35 functions differently. The motion platform attachment mechanism 51 is adapted and configured to lengthen within a plane (e.g., plane a-c) along an axis as well as the ability to change the angle of attachment to both the base 31 and the motion platform 35 such that the end of the motion platform 35 opposing the end adjacent to the static platform 33 can move up or down (along the b axis) so that the plane of the motion platform 35 is at an angle to the plane of the static platform 33 and that these two planes intersect along the line created by their common edge which is a space occupied by the hinging mechanism 73. A radio-paque protractor 74 (shown in FIG. 7B) enables an assessment of movement of the spine during the imaging process.

FIG. 6B represents a side view block diagram of attachment mechanisms and parts of a horizontally configured motion control device 25 in a "front down" configuration. In this configuration, the hinging mechanism 73 functions in the same way allowing for the static platform 33 and motion platform 35 to rotate about the axis c of the hinge such that it changes position from lying within a plane (e.g. c-a plane) to rotating about the c axis. The rigid immobilized static platform/member attachment mechanism 49 in this configuration can be lengthened or shortened, but fixed at a right angle to the platform base 31 and the static platform 33. The motion platform attachment mechanism 51 can be lengthened or shortened such that the angle of attachment to the motion platform 35 and the platform base 31 is no longer a right angle, and instead any other angle dictated by the geometric configuration of the device indicated by the prescriber.

Figure 7B:
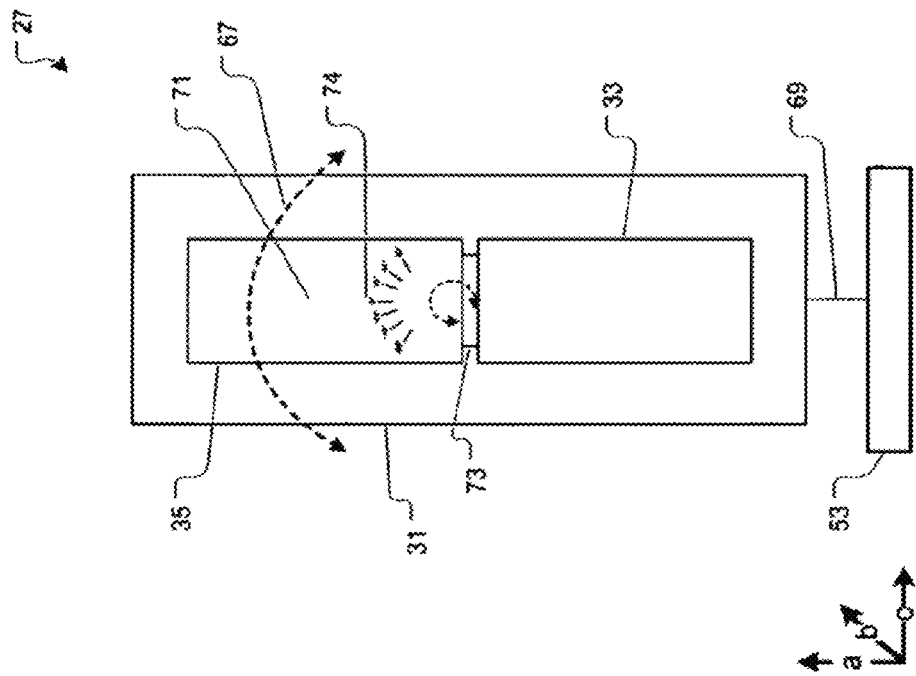
FIGS. 7A and 7B show side and front view block diagrams, respectively, a vertically configured motion control device in a "default" configuration suitable for use with the system disclosed.
Figure 7A:
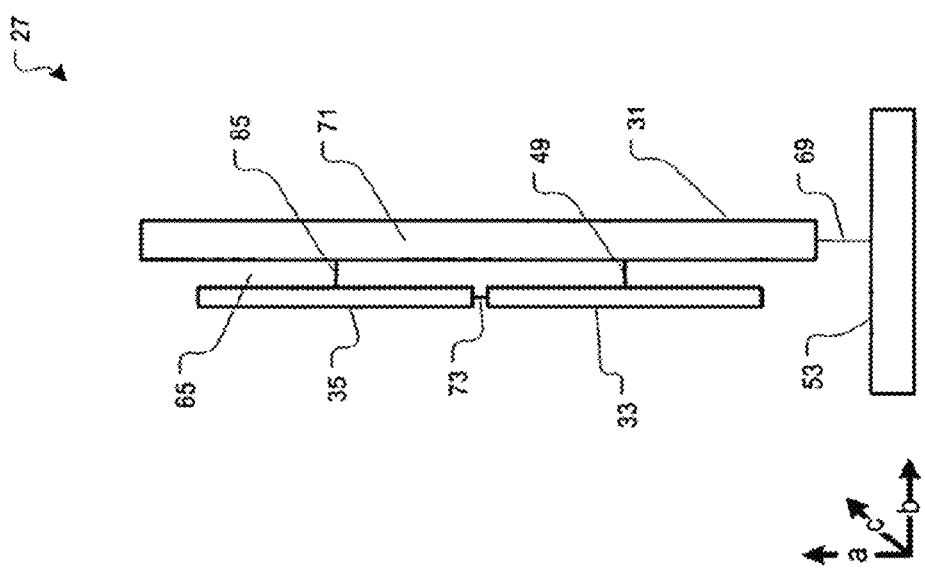
Figure 7C:
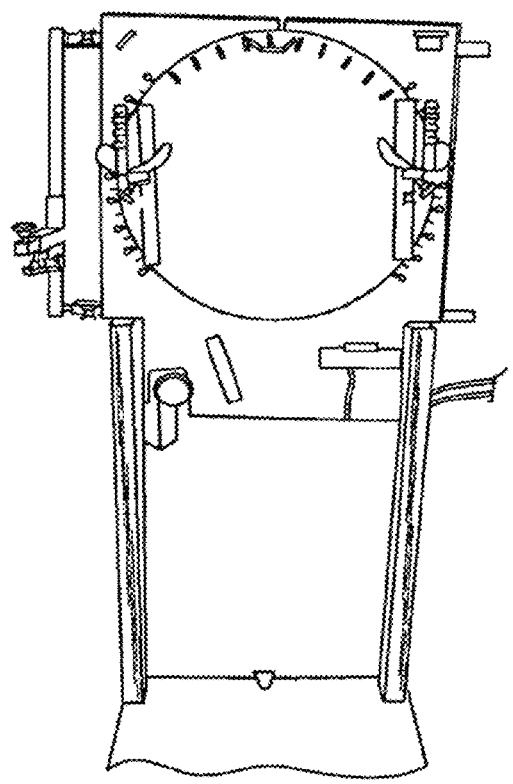
FIGS. 7c-E illustrate a device from different views.
Figure 7D:
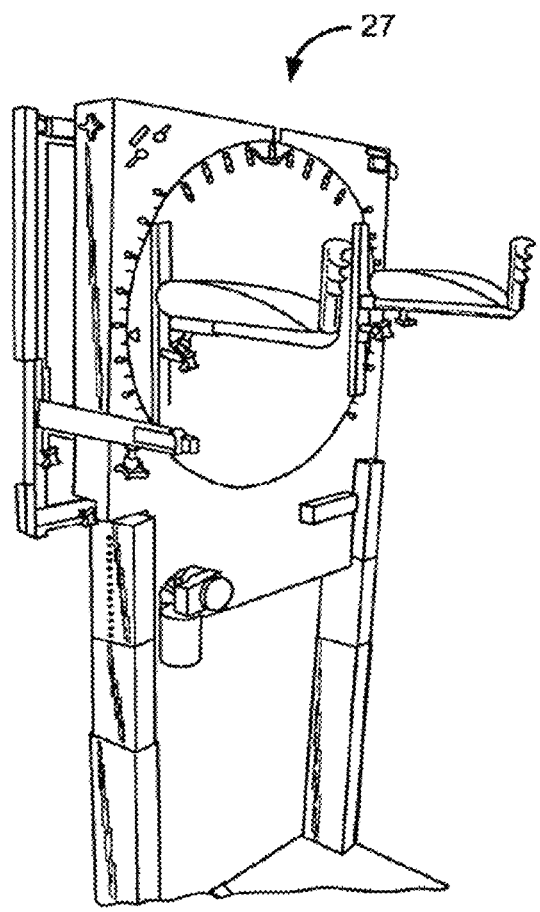
Figure 7E:
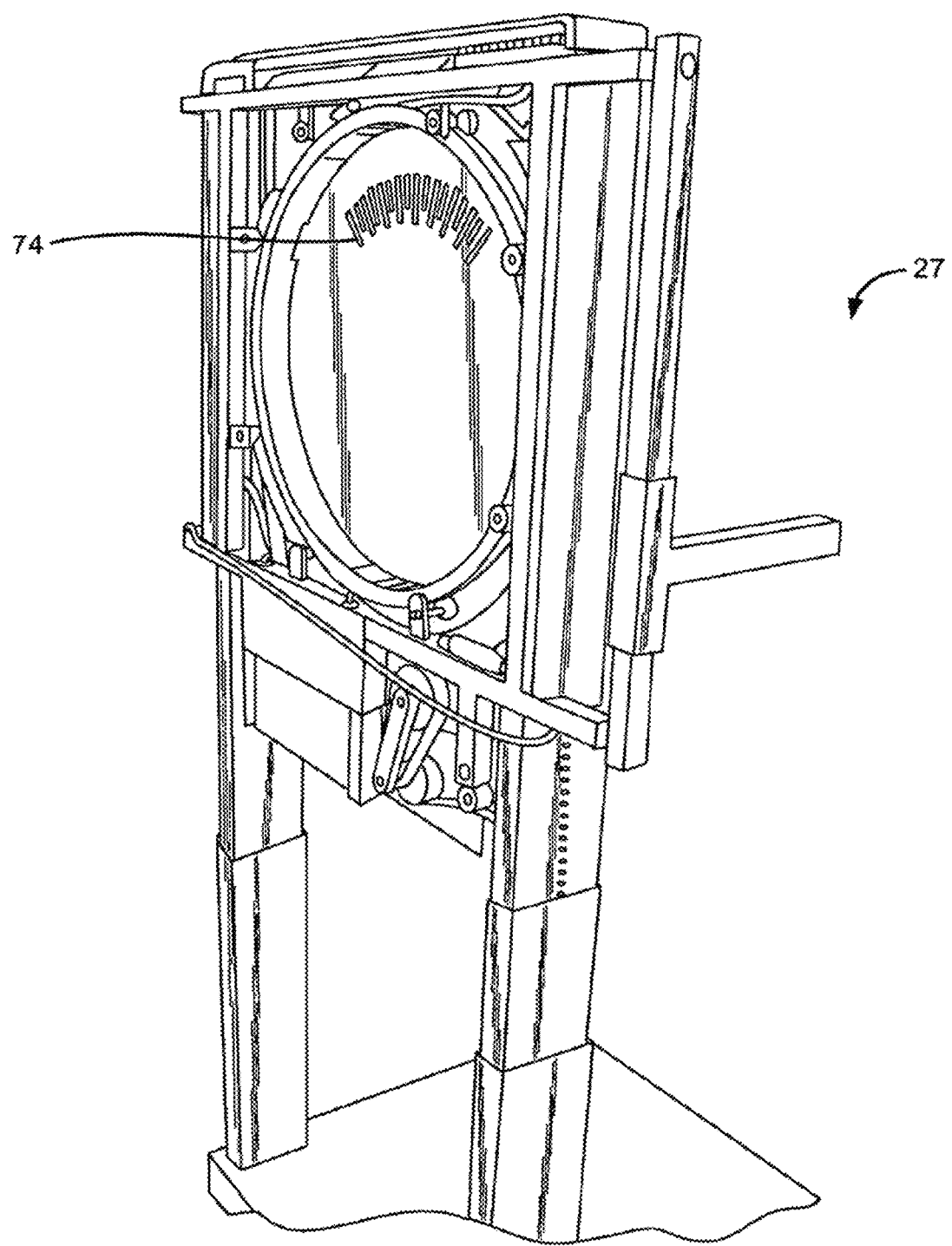

As reflected in FIGS. 7A and 7B, the frame 31 connects to the base 53 of vertically configured motion control device 27 at a rigid base to frame connection mechanism 69. The frame 31 is the frame to which all other sub-systems attach in some way. Moving out from this frame 31, the next two physical sub-systems are the static member 33 and the motion member 35. The frame 31 attaches to the static member 33 by way of a rigid immobilized static platform/member attachment mechanism 49 like the one described for FIGS. 5A and 5B with the added capability of providing cantilevered support for the weight of the static member 33 and any of the attached subject body parts. The frame 31 attaches to the motion member 35 by way of a motion member attachment mechanism 85 that allows free rotation around a fixed axis within the same plane as that of the subject facing surface of the static member, and provides for the cantilevered support for the weight of the motion member 35 and the subject body parts that could be connected to it. The static member 33 and motion member 35 and are attached to each other by the vertically configured motion control device hinging mechanism 73 that when in the "default" position represented in FIGS. 7A and 7B, is locked such that the flat surfaces of both the static member 33 and the motion member 35 reside within the same plane, but still allows for the free rotation of the motion member 35 around a fixed axis within that plane. A radio-opaque protractor 74 adaptable for use with any device disclosed or contemplated to be part of the system is shown on FIG. 7B. FIGS. 7C-E illustrate a configuration of the device.

Figure 9A:
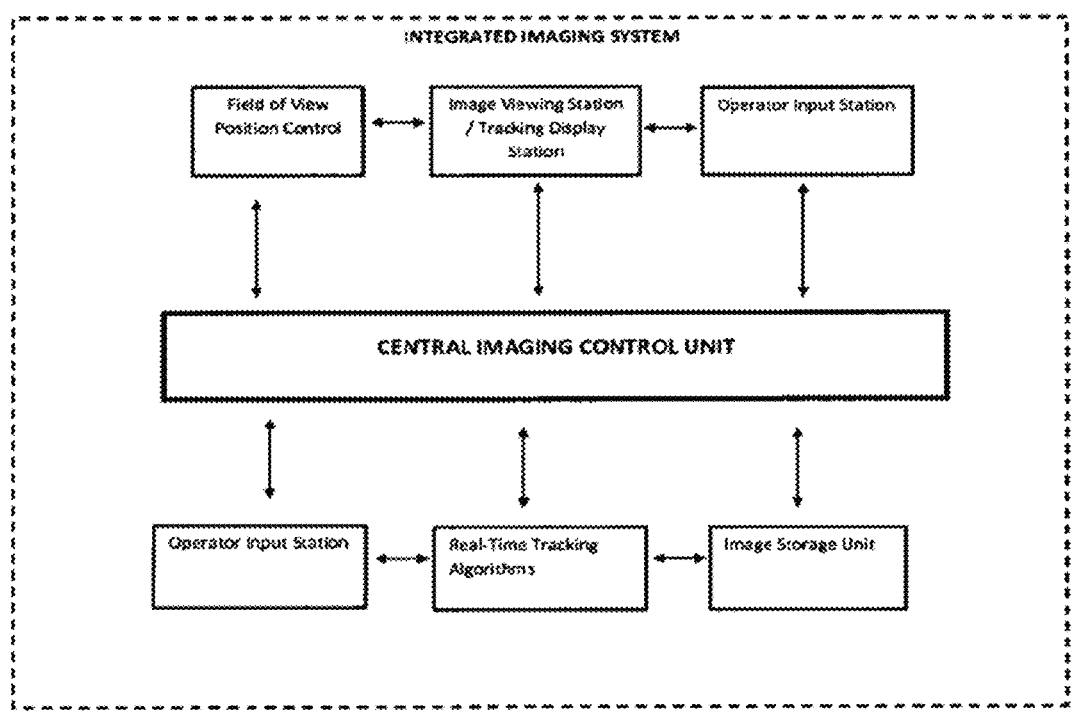
FIG. 9A is a simplified block diagram of the components comprising the integrated imaging system where the imaging apparatus and the tracking apparatus are integrated into the same apparatus and the central processing unit is a part of the apparatus.
Figure 9B:
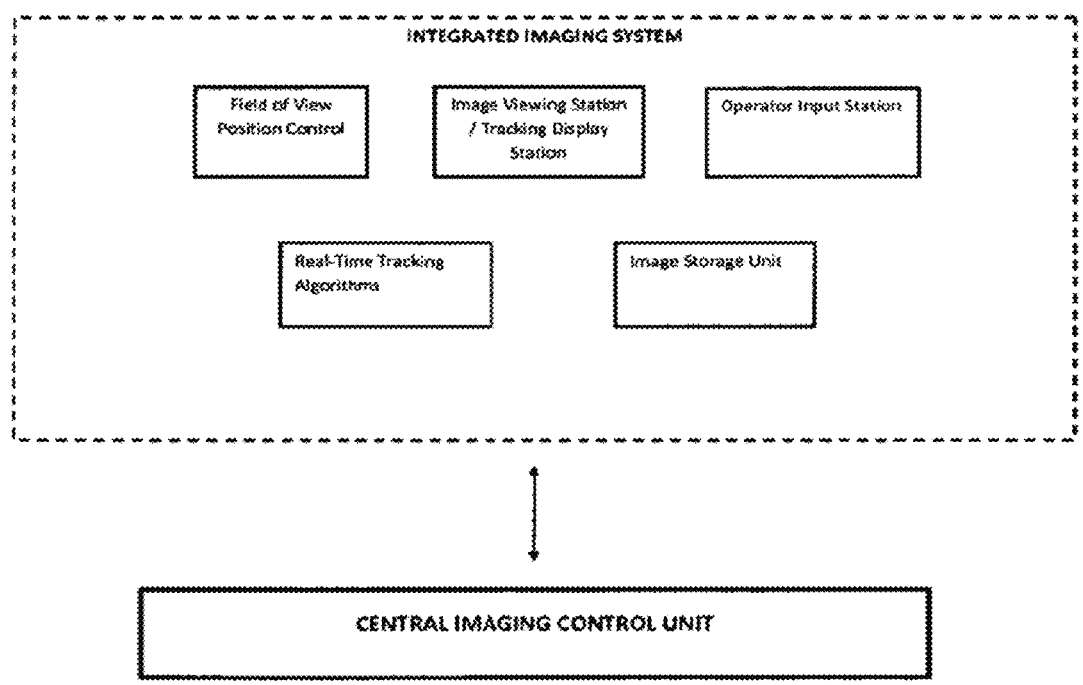
FIG. 9B is a simplified block diagram of the components comprising the integrated imaging system where the imaging apparatus and the tracking apparatus are integrated into the same apparatus and the central processing unit is a separate unit that communicates either wirelessly or through a direct wired connection with the integrated imaging system.
Figure 10:
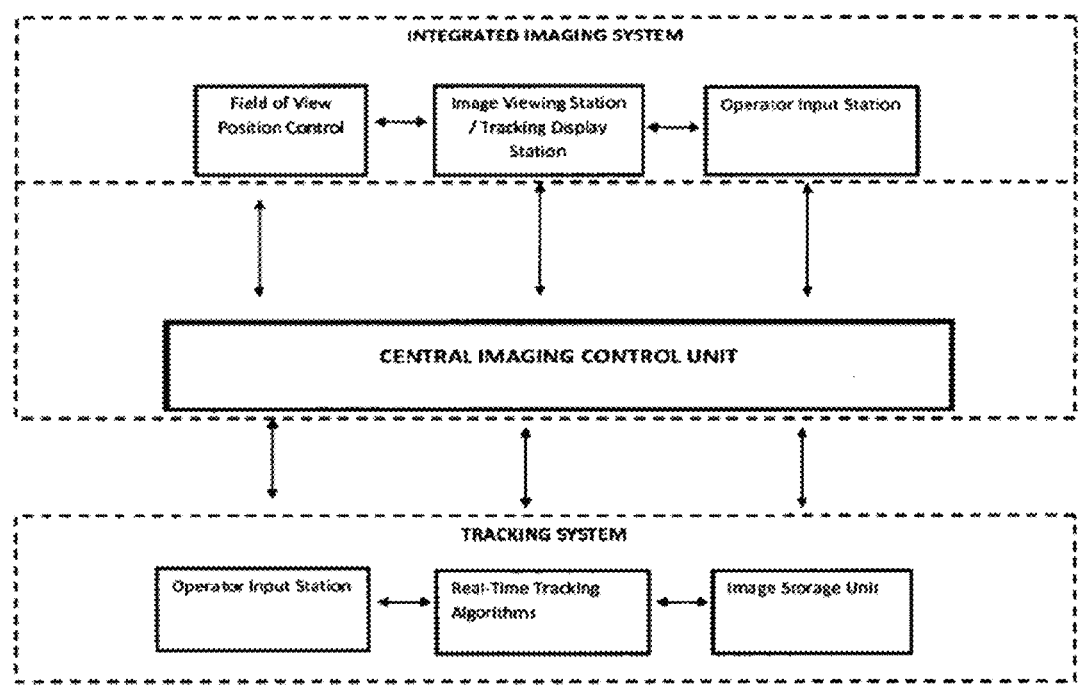
FIG. 10 is a simplified block diagram of the components comprising the integrated imaging system where the imaging apparatus and the tracking apparatus are two separate units and communicate through a central processing unit that communicates with each the imaging and tracking apparatus through a wireless or a direct wired connection.

FIGS. 8A, 8B, and 8C represent the side view block diagram of the vertically configured motion control device 27 in the "default", "top out" and "top in" configurations, respectively. The "default" configuration given in FIG. 9A is as described in the previous paragraph. In FIG. 9B, the "top out" configuration, the attachment mechanism 85 connects the static member 33 to the motion member 35 and can lengthen or shorten along the b axis and/or change the angle of attachment to frame 31 and motion member 35 such that the top of the motion member 35 can move away from the frame 31 so that the plane of the motion member 35 is at an angle to the plane of the static member 33 and that these two planes intersect along the line created by their common edge, the space of which is occupied by the motion control device hinging mechanism 73. Furthermore, the motion member attachment mechanism 85 allows for the free rotation of the motion member 35 around a fixed axis within that plane while providing cantilevered supporting the weight of the motion member and any of the subject's body parts that are connected to it.

In FIG. 8C, the "top in" configuration, the motion member attachment mechanism 85 illustrates its ability to lengthen and shorten along the b axis and change the angle of attachment to the connecting frame 31 and motion member 35. Additionally, in this configuration, the static platform/member attachment mechanism 49 can lengthen along b axis, pushing the static member 33 away from the frame 31 while keeping the static member 33 in a non-changing orientation with respect to the frame 31.

VIII. Software Programs Implementable in the Computing and Network Environments to Achieve a Desired Technical Effect or Transformation FIG. 9 is a simplified block diagram of the integrated imaging system. There is an imaging component, and a tracking component both of which communicate through the central imaging control unit through a series of feedback loops. The imaging component is any suitable imaging device, such as those disclosed above. The tracking component can be any suitable device such as those disclosed above that facilitates tracking and movement of a target patient anatomy.

It is contemplated that the imaging and tracking component are part of the same machine, but it is possible that the imaging and tracking components are separate units connected through either a wireless connection or a direct wire connection to each other or through an external imaging control unit.

The components of the tracking system and the imaging apparatus communicate information through the imaging control unit and the information is used to direct adjustments in real time to the imaging device. The purpose of this invention is to provide the best diagnostic imaging information to the physician and patient and to reduce radiation exposure to the patient and or physician during the testing session The first component of the integrated imaging system is the imaging component. While the following description refers to fluoroscopic imaging in general, it is contemplated that the advantages also applies to many types of diagnostic imaging systems. Further information regarding fluoroscopic devices is provided, for example, in U.S. Pat. No. 6,424,731 for Method of Positioning a Radiographic Device; and U.S. Pat. No. 5,873,826 entitled Fluoroscopy method and X-ray CT apparatus.

Referring to FIG. 9, the basic components of the imaging system are shown. The imaging apparatus includes a central image control unit that controls, among other things, the intensity of the imaging source, the duration of the scan, the optimal frequency of images (frames per second), the position of the imaging source, and the optimal collimation. There is also an image storage unit that acquires the information from the imaging session and stores the image or image sequence for review. There is also an image viewing station for real time viewing of the image or image sequence. The image viewing station also acts as the tracking apparatus monitor where an operator would input information with respect to the area or areas of interest within the field of view of the image.

The components of the diagnostic tracking system are a user input component and computer hardware and software component. While it is contemplated that the tracking display unit is also the image viewing station, those skilled in the art will appreciate that it can also be a separate viewing station independent of the image viewing station and which communicates with the central image control unit either through a secure wireless connection or through a direct wire connection.

The user input component provides the user with the capability of defining one or more areas of interest within the image based on the diagnostic test that is prescribed. In real time, the computer hardware and software component calculates the location of the area of interest and records and communicates this information for several purposes.

One such purpose for the tracking information of the location of the area of interest is for the purpose of acquiring an imaging session that provides optimal diagnostic information and minimal exposure to radiation. This is accomplished through feedback loops to the central image control unit. The information derived from the tracking apparatus direct changes with respect to the imaging session.

For example, one such feedback loop connects a real time, or near real-time, tracking information with the positioning of the x-ray source so as to keep the area of interest within the field of view throughout the imaging session. This is accomplished through either a wireless connection or a direct wire connection that transmits information with respect to the position of the area of interest within the central area of the field of view of the image. The information is received in real time by the central image control unit, processed, and the output is a continuous adjustment to the location of the imaging source with respect to the patient so as to keep the area of interest centered within the field of view throughout the image testing session.

Another feedback loop would use the tracking information to automatically and continuously, or semi-automatically if desired by a user, adjust the collimators so as to direct the radiation to the area of interest and at the same time decrease radiation exposure to the patient. The tracking information transmits information with respect to the location of the area of interest within the field of view of the image to the image control unit through a wireless or a direct wired connection. The image control unit processes the information and automatically and/or continuously adjusts the image settings with respect to the image apparatus collimators. Those skilled in the art will appreciate that this system can be adapted and configured for use with different types of collimators that are already available, and with those that are not yet developed.

Another feedback loop would use the tracking information to adjust the intensity of the radiation so as to produce an image that is sufficiently defined for the purposes of the diagnostic testing requirements. With respect to this feedback loop, the tracking software transmits information either wirelessly or through a direct wired connection to the image control unit. The image control unit then processes the information and automatically and/or continuously adjusts the image settings with respect to intensity of the radiation source. One example of the image source settings that might be adjusted based on the imported information could be the fluoroscopic kv and mA. These types of adjustments might change the contrast levels in the image or reduce noise associated with radiation imaging.

Another feedback loop would transmit the tracking information to the image control unit so as to provide information with respect to the optimal distance of the image intensifier from the patient. The tracking information would be transmitted either wirelessly or through a direct wire connection. The imported information would be processed by the image control unit and direct continuous adjustments to the image intensifier in real time for the purpose of creating the optimal imaging session for the prescribed diagnostic testing session.

Another feedback loop would transmit the tracking information to the image control unit so as to provide information with respect to the optimal fluoroscopic exposure rate at the image intensifier. The tracking information would be transmitted either wirelessly or through a direct wire connection. The imported information would be processed by the image control unit and used to adjust the fluoroscopic exposure rate at the image intensifier continuously and in real time. The rate of exposure with respect to frames per second might depend on the rate at which the area or areas of interest are moving during the testing session.

For all of these situations, more accurate information with respect to image source location, intensity and collimation will reduce radiation exposure to both the patient and to the operator. It is contemplated that there are other aspects of the imaging session that can be continuously adjusted in real time during the imaging session so as to improve the quality of the images, create the optimal imaging environment, produce the best diagnostic imaging information and minimize the radiation exposure to the patient.

As will be appreciated by those skilled in the art, for all of these feedback loops automatically and continuously communicating instructions based on the feedback loops and the images can include, for example, transmitting a new instruction which changes one or more settings, transmitting an instruction which maintains the most recent one or more settings, transmitting an instruction that repeats an earlier one or more instructions, or providing no change in instruction in current instructions. Where no change instructions are provided, the system and/or one or more feedback loops can be adapted and configured to automatically repeat the most recent instructions after a lag of a set amount of time from providing the image data for analysis. Thus for example, if a feedback loop is processed and a period of n seconds passes the prior setting will remain in place.

IX. Examples

Figure 11:
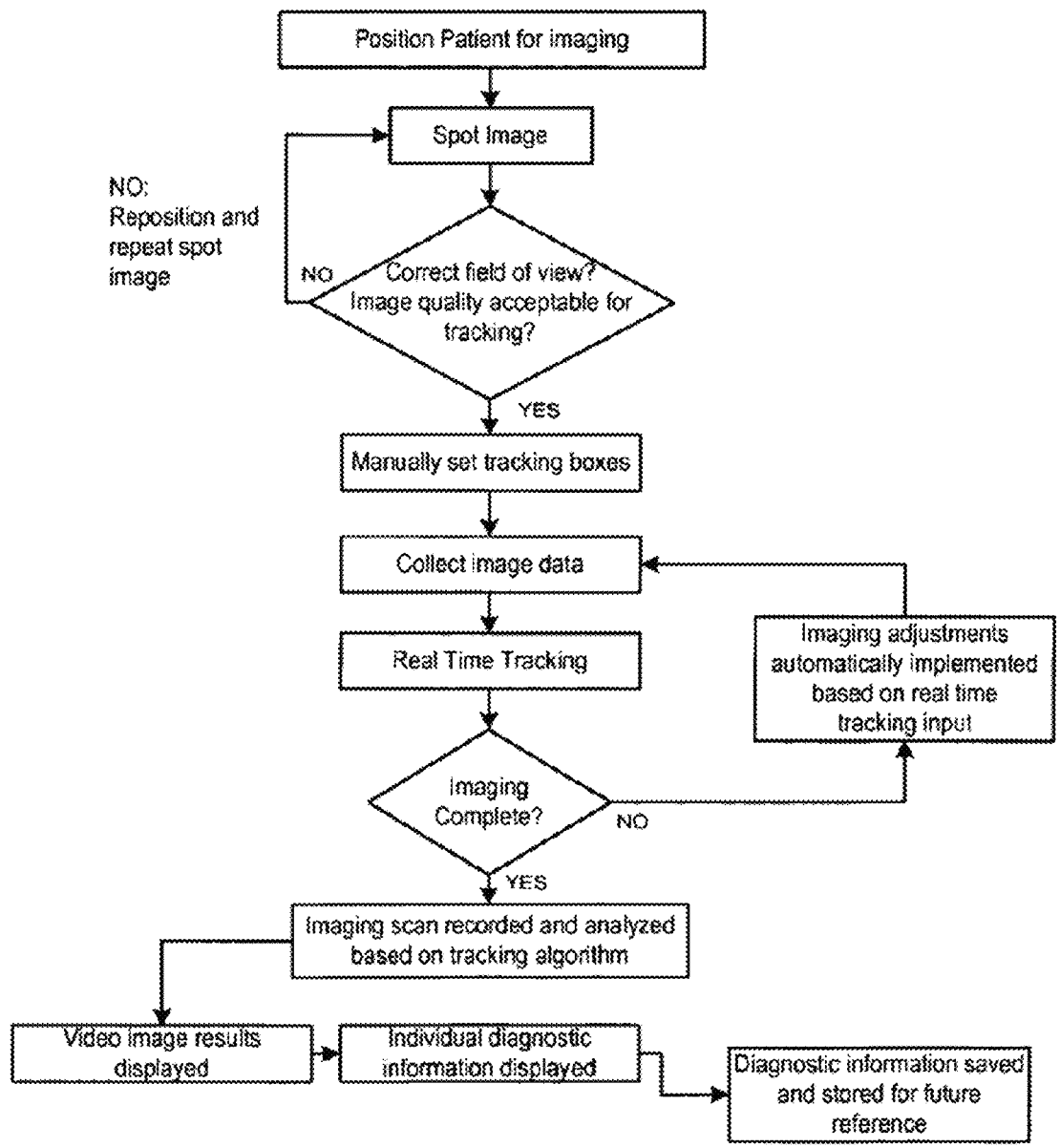
FIG. 11 is a flow chart of the process by which the integrated imaging system operates.

A process by which this disclosure can be implemented is shown in FIG. 11. The process begins with the patient being positioned in the starting position for the prescribed imaging test. A spot image is acquired. The operator or physician determines whether the spot image captures the field of view necessary for the prescribed imaging test. If the patient is not in the correct position, the operator or physician will reposition the patient and repeat the process. Once the area of interest for the prescribed imaging test is within the field of view of the image, the operator or physician will manually defined the area of interest. For example, this could be defining one or more vertebra of the spine for a flexion extension testing session. Once the areas of interest are defined, the imaging session begins. During the imaging session, the tracking apparatus tracks the area or areas of interest within the image in real time. The information with respect to image quality and position of the area or areas of interest are communicated from the tracking apparatus to the central imaging control unit. The central imaging control unit processes the information in real time, and automatically and continuously adjusts the imaging apparatus so as to maintain optimal imaging settings for the prescribed testing session. At the completion of the imaging testing session, the image results are displayed both as a video of the imaging session and the quantitative diagnostic information is also displayed. Finally, the information is stored and can be recovered for future reference.

It is contemplated that this apparatus can incorporate the use of many different external devices that might be used in conjunction with a diagnostic imaging session. For example, if an apparatus that controls the motion of the patient during the testing session is used, the information from that device will also communicate with the central imaging control unit and implement the same feedback loops as described above. The motion apparatus can be used in conjunction with the imaging system as a means of standardizing or supporting patient motion during the imaging session. The motion apparatus is comprised of a patient motion control unit that interacts and moves a patient undergoing an imaging session in a controlled, predetermined motion path. It is contemplated that the motion apparatus communicates information with the imaging device with respect to the position of the table and/or the patient on the table during imaging. It is also contemplated that the motion apparatus can adjust based on the position of the imaging device. The motion table may adjust for example to maintain the same image field of view throughout the motion testing session. It is possible for each component of the motion apparatus to communicate or receive information through a central processing unit.

While the previous description describes a motion control device used in conjunction with the integrated imaging system, those skilled in the art will appreciate that this is only one example, and there are many types of external apparatus' that can be used during an imaging session, and it is contemplated that each such device could be incorporated into this invention.

Functional tests of a target subject anatomy, such as the spine, can be performed to minimize the radiation dose involved during a procedure with an imaging procedure based on real-time or near real-time feedback. A patient would be positioned on the articulating patient handling device and prepared for an imaging study. The imaging study would involve the capturing of images of the lumbar spine with a standard hospital fluoroscope, which is capable of capturing moving x-ray type video images of the lumbar spine. The fluoroscope would then begin recording images as the patient handling device affects a controlled movement of the subject during the imaging session. During a traditional imaging session, the field of imaging for standard fluoroscopes is typically a 9 or a 12 inch circle. For a lumbar vertebrae of interest the vertebra only occupies a small subset of this imaging field—on the order of 15-30% of the imaging field—however the entire imaging field is being irradiated and imaged. By providing a real-time or near real-time tracking system the exact position and trajectory of the target anatomy can be determined, then fed back into a collimator. The collimator would then be placed on the X-ray generator, and would be able to adjust the shape and trajectory of the collimation of the X-ray beam according to data received from the tracking system to prevent regions other than those of interest (i.e. the lumbar vertebral bodies) from being irradiated and imaged. The data capture, analysis and feedback loop would then reduce the overall radiation dose to the patient proportional to the proportion of the beam that is being collimated.

Yet another example provides an improved functional test of a target anatomy allows smaller image intensifiers to be used. Currently, as discussed above, standard hospital fluoroscopes have a 9 or a 12 inch image intensifier, and therefore a corresponding 9 or 12 inch field of view. When imaging the lumbar spine in motion, it is often the case that, in the case when a subject is moving their torso to affect a lumbar bend, superior lumbar vertebrae such as L1 or L2 move out of the 9 or 12 inch field of view as a patient approaches a maximum lumbar bending angles. Real-time or near real time adjustments to the anatomy contained within the field of view would make it possible to prevent or minimize the target anatomy from exiting the field of view during imaging through a movement sequence.

Two different mechanisms can be provided to prevent or eliminate movement of the target anatomy from the field of view. By providing a real-time tracking capability that allows a computer implemented system to precisely monitor the position of the vertebral bodies during imaging, the present invention provides for a feedback loop from the real time tracking system to either the positioning system for the fluoroscopy or the positioning system on which the articulating patient handling device rests. By making adjustments to either the position of the image intensifier and/or to the articulating patient handling device assembly, it would be possible to maintain all anatomy of interest within the field of view at all points during the movement and prevent any anatomy from exiting the field of view. The effect of this is that less expensive fluoroscopy systems with smaller image intensifiers would be suitable for conducting imaging of, for example, the lumbar spine during controlled lumbar bending.

A problem associated with functional test of the spine is variability. Clinical studies that have shown that there can be a wide degree of variability in measurement of in vivo lumbar vertebral motion. One system to reduce the variability is to standardize the bending angle to which subjects bend during imaging. However even when standardizing bending angle, there can still be variability with respect to the total amount of lumbar bending that is occurring during a particular imaging session. The total amount of lumbar bending that is occurring can be measured by measuring the angulation between L1, the uppermost (or most superior) lumbar vertebra, and S1, the lowermost (or most inferior) lumbar vertebra. This overall L1-S1 angulation is measured by comparing two X-ray or fluoroscopic images of a subject taken from two different positions. For example, a subject might perform a gross lumbar bend and achieve 60 degrees of gross lumbar bending, but the L1-S1 angulation might only by 45 degrees. The difference is attributable to mechanical slack in other anatomy involved in the motion, such as the hips, thorax, arms, shoulders, etc. By standardizing the overall L1-S1 angulation of a subject instead of the motion control device, and by taking measurements of the motion of individual vertebral bodies at standardized L1-S1 angles as opposed to standardized gross bending angles, it is possible to further reduce intervertebral angulation measurement variability. Therefore an advantage afforded by the present invention would be to have subjects bend to a standardized L1-S1 angle, letting the overall gross bending angle vary, as opposed to bending subjects to a standardized gross bending angle and letting the L1-S1 angle vary. The real-time or near real-time feedback loop from the tracking system to the articulation control system of the patient handling device enables the device to discontinue imaging when an actual patient bending angle has been achieved. Such a feedback loop would allow a diagnostician to select a range of motion and then for the subject to be guided through a standard bend that would continue until a selected or specified L1-S1 angle was achieved. The real time tracking system would provide the means of signaling to the articulation control system that the subject has achieved a specific L1-S1 angle, and therefore that bending should be stopped and reversed in the opposite direction to return the subject to a neutral position. Such a system would provide the capability to produce lower variability intervertebral angulation measurements.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system measuring skeletal joint motion in a subject comprising:
   a) a motion device adapted and configured to continuously move a joint of the subject, the motion device comprising:
      a platform base, and
      a motion platform further comprising a static platform connected to an upper surface of the platform base, a movable platform connected to at least one of the static platform or an upper surface of the platform base, wherein the static platform is adjacent the movable platform wherein movement of the movable platform is achieved in operation by a motor in communication with the moveable platform;
   b) an imaging device in communication with the motion device adapted and configured to obtain imaging data; and
   c) a computing system adapted and configured to analyze the obtained imaging data to generate an instruction and then communicate the instruction to at least one of the motion device and the imaging device wherein the computing system is configurable to
      receive information from at least one of the motion device and the imaging device during an imaging session;
      analyze the received information during the imaging session;
      determine whether a target anatomy is within a field of view during the imaging session;
      evaluate a position of the imaging device, a position of the motion device, a radiographic imaging technique, and a geometric configuration of a collimator;
      determine whether a change to one or more of a position of the imaging device, a position of the motion device, a radiographic imaging technique, and a geometric configuration of a collimator will bring the target anatomy within the field of view; and instruct at least one of the motion device and imaging device to change an imaging environment automatically and continuously during the imaging session to maintain the target anatomy within a field of view by one or more of changing the position of the imaging device, changing the position of the motion device, changing the radiographic imaging technique, and changing the geometric configuration of the collimator.

2. The system of claim 1, wherein the imaging device is an X-ray tube and image intensifier with dosage control.

3. The system of claim 1, wherein the imaging device is a magnetic resonance scanner.

4. The system of claim 1, wherein the platform is a laterally moveable platform.

5. The system of claim 1, wherein the movable platform is situated on a support which lies on the upper surface of the platform base.

6. The system of claim 5, wherein the imaging device is an X-ray tube and image intensifier with dosage control.

7. The system of claim 6, wherein the imaging device is a magnetic resonance scanner.

8. The system of claim 1, further comprising a control arm for driving movement of the moveable platform.

9. The system of claim 1 further comprising a processing system.

10. The system of claim 1 wherein the motion device is adapted to communicate motion information to the imaging device during use.

11. The system of claim 1 wherein continuous adjustments are made to an imaging environment.

12. The system of claim 11 wherein the instruction changes an aspect of an imaging field.

13. The system of claim 11 wherein the instruction changes a movement of a motion device.

14. The system of claim 1 wherein a range of motion of the motion device is based on a selected target motion for a patient.

15. The system of claim 1 wherein a range of motion of the device is based on a gross motion of a patient.

* * * * *